(12) United States Patent
Kumar et al.

(10) Patent No.: US 8,653,328 B2
(45) Date of Patent: Feb. 18, 2014

(54) PLANT GENES ASSOCIATED WITH SEED OIL CONTENT AND METHODS OF THEIR USE

(75) Inventors: Rajesh Kumar, New Delhi (IN); Henry T. Nguyen, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 214 days.

(21) Appl. No.: 12/972,408

(22) Filed: Dec. 17, 2010

(65) Prior Publication Data

US 2011/0191904 A1    Aug. 4, 2011

Related U.S. Application Data

(60) Provisional application No. 61/287,572, filed on Dec. 17, 2009, provisional application No. 61/328,545, filed on Apr. 27, 2010.

(51) Int. Cl.
*C12N 15/87* (2006.01)
*C12N 15/82* (2006.01)
*C12N 15/29* (2006.01)
*A01H 5/00* (2006.01)

(52) U.S. Cl.
USPC ......... 800/281; 800/306; 800/312; 800/320.1

(58) Field of Classification Search
None
See application file for complete search history.

(56) References Cited

U.S. PATENT DOCUMENTS

| 7,790,953 B2 | 9/2010 | Fillatti et al. | |
|---|---|---|---|
| 2004/0034888 A1 * | 2/2004 | Liu et al. | 800/289 |
| 2008/0184393 A1 | 7/2008 | Zhang et al. | |

OTHER PUBLICATIONS

Kumar et al 2006 The Plant Journal 48: p. 920-932.*
Sayanova et al 1997 PNAS 94: p. 4211-4216.*
Napier JA, et al: A new class of cytochrome b5 fusion proteins. Biochem J 1997, 328: 717-720.
Smith MA, et al: Evidence for cytochrome b5 as electron donor in ricinoleic acid biosynthesis in microsomal preparations from developing castor bean (*Ricinus communis* L.). Biochem J 1992, 287: 141-144.
Broadwater JA, et al: Desaturation and hydroxylation. Residues 148 and 324 of *Arabidopsis* FAD2, in addition to substrate chain length, exert a major influence in partitioning of catalytic specificity. J Biol Chem 2002, 277: 15613-15620.
Kumar R, et al: A mutation in *Arabidopsis* cytochrome b5 reductase identified by high throughput screening differentially affects hydroxylation and desaturation. Plant J 2006, 48: 920-932.
Cahoon EB, et al: Formation of conjugated Δ8, Δ10-double bonds by Δ12-oleic-acid desaturase related enzymes. J Biol Chem 2001, 276: 2637-2643.
Nam JW, Kappock TJ: Cloning and transcriptional analysis of Crepis alpine fatty acid desaturases affecting the biosynthesis of crepenynic acid. J Exp Bot 2007, 58: 1421-32.
Nagano M, et al: Functional association of cell death suppressor, *Arabidopsis* Bax inhibitor-1,with fatty acid 2-hydroxylation through cytochrome b5. Plant J 2009, 58: 122-134.
de Vetten N, et al: A cytochrome b5 is required for full activity of flavonoid 3',5'-hydroxylase a cytochrome P450 involved in the formation of blue flower colors. PNAS 1999, 96: 778-783.
Fan RC, et al: Apple sucrose transporter SUT1 and sorbitol transporter SOT6 interact with Cytochrome b5 to regulate their affinity for substrate sugars, Plant Physiol 2009 150:1880-1901.
Ohlrogge J, Browse J: Lipid biosynthesis. Plant Cell 1995, 7: 957-970.
Miquel M, Browse J: *Arabidopsis* mutants deficient in polyunsaturated fatty acid synthesis. Biochemical and genetic characterization of a plant oleoyl-phosphatidylcholine desaturase. J Biol Chem 1992, 267: 1502-1509.
Fukuchi-Mizutani M, et al: Microsomal electron transfer in higher plants: cloning and heterologous expression of NADH-cytochrome b5 reductase from *Arabidopsis*. Plant Physiol 1999, 119: 353-362.
Hwang YT, et al: Novel targeting signals mediate the sorting of different isoforms of the tail-anchored membrane protein cytochrome b5 to either endoplasmic reticulum or mitochondria. Plant Cell 2004, 16: 3002-3019.
Mitchell AG, Martin CE: A novel cytochrome b5-like domain is linked to the carboxyl terminus of the *Saccharomyces cerevisiae* Δ-9 fatty acid desaturase. J Biol Chem 1995, 270: 29766-29772.
Sayanova O, et al: Expression of a borage desaturase cDNA containing an N-terminal cytochrome b5 domain results in the accumulation of high levels of Δ6-desaturated fatty acids in transgenic tobacco. PNAS 1997, 94: 4211-4216.
Covello PS, Reed DW: Functional expression of the extraplastidial *Arabidopsis thaliana* oleate desaturase gene (Fad2) in *Saccharomyces cerevisiae*. Plant Physiol 1996, 111: 223-226.
Reed EW, et al: Characterization of the *Brassica napus* extraplastidial linoleate desaturase by expression in *Saccharomyces cerevisiae*. Plant Physiol 2000, 122: 715-720.
Dyer JM, et al: Chilling-sensitive, post-transcriptional regulation of a plant fatty acid desaturase expressed in yeast. Biochem Biophys Res Commun 2001, 282: 1019-1025.
Vrinten P, et al: Two FAD3 desaturase genes control the level of linolenic acid in flax seed. Plant Physiol 2005, 139: 79-87.

(Continued)

*Primary Examiner* — Brent T Page
*Assistant Examiner* — Matthew Keogh
(74) *Attorney, Agent, or Firm* — Lathrop & Gage LLP; Dan Cleveland, Jr.

(57) ABSTRACT

Cytochrome b5 (Cb5) is a haem-binding protein located in the endoplasmic reticulum (ER) and the outer mitochondrial membranes of higher eukaryotes. In higher plants, animals, and fungi, the ER resident Cb5 has been shown to play a role in desaturation of acyl CoA fatty acids. Higher plants Cb5 isoforms from plants such as soybean or *Arabidopsis* are capable of modulating omega-3 desaturation. Co-expression of certain Cb5 isoforms with FAD3 in a host plant results in increased production of seed oil content as well as altered ratio between different fatty acids. It is also disclosed here that overexpression of *Yarrowia* ACL enzymes in the plastids of a host plant helps boost the synthesis of acetyl CoA, which in turn, may lead to increased synthesis of fatty acids and enhanced oil accumulation in the seeds.

8 Claims, 12 Drawing Sheets

(56) References Cited

OTHER PUBLICATIONS

Dyer JM, Chapital DC, Kuan JC, Mullen RT, Turner C, McKeon TA, Pepperman AB: Molecular analysis of a bifunctional fatty acid conjugase/desaturase from tung. Implications for the evolution of plant fatty acid diversity. Plant Physiol 2002, 130: 2027-38.

Shockey JM, et al: Cloning, functional analysis, and subcellular localization of two isoforms of NADH:cytochrome b5 reductase from developing seeds of tung (*Vernicia fordii*). Plant Sci 2005, 169: 375-385.

Maggio C, et al: Intracellular sorting of the tail-anchored protein cytochrome b5 in plants: a comparative study using different isoforms from rabbit and *Arabidopsis*. J Exp Bot 2007, 58: 1365-1379.

Shoemaker RP, et al: A compilation of soybean ESTs: generation and analysis. Genome 2002, 45: 329-338.

Shoemaker RC, et al: Paleopolyploidy and gene duplication in soybean and other legumes. Curr Opin Plant Biol 2006, 9: 104-109.

Tang GQ, et al: Oleate desaturase enzymes of soybean: evidence of regulation through differential stability and phosphorylation. Plant J 2005, 44: 433-446.

Petrini GA, et al: *Trypanosoma brucei* oleate desaturase may use a cytochrome b5-like domain in another desaturase as an electron donor. Eur J Biochem 2004, 271: 1079-1086.

Broun P, et al: Catalytic plasticity of fatty acid modification enzymes underlying chemical diversity of plant lipids. Science 1998, 282: 1315-1317.

Kajiwara S, et al.: Polyunsaturated fatty acid biosynthesis in *Saccharomyces cerevisiae*: Expression of ethanol tolerance and the FAD2 gene from *Arabidopsis thaliana*, Appl Env Microbiol 1996, 62: 4309-4313.

Bilyeu KD, et al.: Three microsomal omega-3 Fatty-acid desaturase genes contribute to soybean linolenic acid levels Crop Sci 2003, 43: 1833-1838.

Smith MA, et al: Electron-transport components of the 1-acyl-2-oleoyl-sn-glycero-3-phosphocholine $\Delta$12-desaturase ($\Delta$12-desaturase) in microsomal preparations from developing safflower (*Carthamus tinctorius* L.) cotyledons. Biochem J 1990, 272: 23-29.

Dyer JM, Mullen RT: Engineering plant oils as high-value industrial feedstocks for biorefining: the need for underpinning cell biology research, Physiol Plant 2008, 132: 11-22.

Sambrook J, et al: Molecular Cloning: A laboratory manual, 2nd edn. 1989, New York: Cold Spring Harbor Laboratory Press.

Larkin MA, et al: Clustal W and Clustal X version 2.0. Bioinformatics 2007, 23:2947-2948.

Tamura K, et al: MEGA4: Molecular evolutionary genetics analysis (MEGA) software version 4.0. Mol Biol Evolution 2007, 24: 1596-1599.

Rangasamy and Ratledge (2000) Genetic Enhancement of Fatty Acid Synthesis by Targeting Rat Liver ATP:Citrate Lyase into Plastids of Tobacco.Plant Physiology, 122: 123138.

Cahoon et al. (1992) Expression of a coriander desaturase results in petroselinic acid production in transgenic tobacco. PNAS, 89:11184-88.

Cahoon, EB (2003) Genetic Enhancement of Soybean Oil for Industrial Uses: Prospects and Challenges. AgBioForum, 6(1&2): 11-13.

Damude et al., (2006) Identification of bifunctional delta 2/omega-3 fatty acid desaturases for improving the ratio of omega3 to omega6 fatty acids in microbes and plants. PNAS, 103: 9446-9451.

* cited by examiner

```
                    1                                                                          80
AtCb5-A      (1)  -MSDRKVLSFEEVSKHNKIKDCWLIISGKVYDVTPFMDDHPGGDEVLLSSTGKDAINDFEDVGHSDIARDMDKYETGE
TungCb5-A    (1)  -MASDPKTHKFEDVKVHNKIKDCWLIISGKVYDVTPFNEDHPGGDEVLLSSTGKDAINDFEDVGHSDSARDNMEKYYIGE
GmCb5-A1     (1)  -MASDRKLHTFEEVAKHNQTKDCWLIISGKVYDVTPFNEDHPGGDEVLLSATGKDAINDFEDVGHSDSARDMEKYTIGE
GmCb5-A2     (1)  -MASDRKIHTFEEVAKHDQTKDCWLISGKVYDVTPFNEDHPGGDEVLLSATGKDAINDFEDVGHSDSARDMEKYYIGE
AtCb5-B      (1)  -MGGDGKVFTLSEVSQHSSAKDCWIVIDGKVYDVTKFLDDHPGGDEVLLTSIGKDATDDFEDVGHSTAKAMLDEYYVGD
TungCb5-B    (1)  -MGGDMKKVFTLAQVSQHNNVSQHNEKIIDGKVYDVIKFLEDHPGGDEVLLSSTGKDATDDFEDVGHSLSAREAMDQYYVGE
AtCb5-E      (1)  -MGDEAKIFTILSEVSEHNQAHDCWIVINEKVYNVTKFLEDHPGGDEVLLSSTGKDATDDFEDVGHSESAREMEQYYVGE
GmCb5-E1     (1)  -MGGERNKVFSLAEVSQHNNAKDCWIVIHEKVYNVTKFLEDHPGGDEVLLSSTGKDATNDFEDIGHSTSAVAMDEFYVGD
GmCb5-E2     (1)  -MGGERNKVFTLAEVSQHNNAKDCWIVIHGKVYNVTKFLEDHPGGDEVLLSSTGKDATNDFEDIGHSTSAVAMMDEFYVGD
TungCb5-C    (1)  -MGSS-GKVFTLAEVSEHNNPKDCHLVIEGKVYDVKFLEDHPGGDEVLLSATGKDATDFEDVGHSSSARAMDEFYVGE
AtCb5-C      (1)  -----MANLISFHDVAKHKCENDGWIIIHGKVYDISTFMDEHPGGDNVLLAVTGKDASIDFEDVNHSKDAKEIMKKYCIGD
GmCb5-C1     (1)  -MGSKTKTFEEVAKHNHRKDCWIVIVGKVYDVTPFLDDHPGGDEVIWTAIEKDATTDFEDIGHSDSATQMEKYEVGE
GmCb5-C2     (1)  -MGSKIKIFTEEVAKHNHRKDCWIIIVGKVYDVTPFLDDHPGGDEVIWTAIEKDATTDFEDIGHSDSAIEMMEKYEIGK
GmCb5-C3     (1)  -MASNPKTLIFEEVAKHNNKDCWIIINGKVYDITPFLDEHPGGDEVIWTSIGKDATIDFEDVGHSDAIDEFEDVGHSDATIDEEDVGHSDATIDFEDVGHSDAIEMMEKYEIGK
GmCb5-C4     (1)  -MASNPKLIFEEVANHNNKKDCWIIINEKVYDITPFLDEHPGGDEVIWTSTGKDATIDFEDVGHSDATIEMMEKYFVGK 81                                    TMD                              147
AtCb5-A      (80) IDSSSVPATRT----YVAPQQ---PAYNDKTDEFFIKILQFFIKILQFLVPLILGLALVVRHYTKKD------
TungCb5-A    (80) IDSSTVPANRT----HIPPK---QVYNQDKSEFFIKILQFLVPLLIIGLIAFAVRHTKKE------
GmCb5-A1     (80) IDSSTVPLKRT----YIPPQQ--AQYNDPDKTPEFVIKILQFLVPLLIIGLLIGLAFVVRHYTKKE------
GmCb5-A2     (80) IDSSTVPLKRT----YIPPQQ--AQYNPDKTPEFVIKILQFLVPLLIIGLLIGLAFVVRHYTKKE------
AtCb5-B      (80) IDTATVPVEGK----EVPPTSIKAVAIQDKSSDFVIKILQFLVPLLIIGLAFGIRYYIKIKAPSS-----
TungCb5-B    (80) IDPSTVPKKGH----YKPPK---QPHYNQDKTSEFIIKLLQFLVPLLIIGLAFGIRLYTKST------
AtCb5-E      (80) IDETTIPKKVK----YTPPK---QPHYNQDKMPEFIIRILQFLVPLFTIGLAVGIRFYIKST------
GmCb5-E1     (81) IDTSIIPSEVK----YTPPK---QPHYNQDKTPEFIIKILQFLVPLFIIGLAVGIRFYIKST------
GmCb5-E2     (81) IDTSIIPSEVK----YTPPK---QPHYNQDKTPEFIIKILQFLVPLFIIGLAVGIRFYIKST------
TungCb5-C    (77) IDSSSIPSRMA----YTPPK---QPHVNQDKTMEFIIKFLQFVVPLLIIGLAVGIVAFALRFYNNK-----
AtCb5-C      (80) VDQSTVPVTQQ---YIPPWEKESTRAFT EESGKWLIYLIPLLILGVAFALRFYNNK---SEN
GmCb5-C1     (80) VDIWTIPAQVT SSSSVRPPTQAP-VYNNQSGFWWIIQYIVPLLIIAFAFGLQYGKKSK---SEN
GmCb5-C2     (80) VDITTIPAQVI SNNSVROPTQAPFAYNNQSGFWVKMIQYIVPLLIIAFAFGQYGKKMNKSTESEN
GmCb5-C3     (80) VDTSTIPPKVS---HSLPQPTQTH-GAGNCGSGFVVKILQFLLEPLLLGLAFALVYGQKKHASTS----
GmCb5-C4     (80) VDTSTIPAKVM---HSLPQPTQAG-GAGNCGSGFWVKILQFLILGLAFAIMYGKKKHASTS----
```

FIG. 8

The deduced amino acid sequence of soybean Cb5 (GmCb5) isoforms were aligned with known and putative ER targeted Cb5 proteins of Tung and Arabidopsis using vector NTI software. Accession number of soybean Cb5 is provided in Table1. Accession number of Arabidopsis Cb5: AtCb5-A (At5g53560), AtCb5-B (At5g48810), AtCb5-C (At2g46650) and AtCb5-E (At2g32720). Accession number of Tung Cb5: TungCb5-A (AY578727), TungCb5-B (AY578728) and TungCb5-C (AY578729). The depiction of transmembrane domain (TMD) is based on an earlier report [19].

Cb5-A1:
atggcttcagatcggaaacttcacacttttgaggaggtggcaaagcacaaccagaccaaggattgctggctcatcatttctggcaaggt
gtatgatgtcaccccttcatggaggatcatcccggaggtgatgaggttttgttatctgcaacagggaaagatgcaaccaatgactttga
agatgtggggcacagtgattctgctagagatatgatggaaaaatactacattggtgagattgatgcatcaaccgtcccactaaaacgg
acctacattccacctcagcaagctcagtacaatcctgataagactccagaatttgtgatcaagattttgcagttcctggtccctctcctgat
cttgggcttggcctttgttgtgcgacactacaccaagaaagagtag

Cb5-C2:

atgggttcaaaaaccaagactttaccttgaagaggtggctaaacacaatcacaggaaggattgttggattatagtcaaagggaagg
tgtatgatgtcaccccattttggatgatcatccaggaggtgatgaagttttagtgactgcaacagagaaggatgccaccactgattttga
agatattggccacagtgattcagcaacacagatgatggaaaaatactttgttggggaggttgacaccaacactcttccagcacaagtt
accagcaacaacagtgtacgccaaccaacacaagcaccacctgcctataacaatcaatcttcaggatttgttgtgaagatgttgcagt
acatagtgccattgctgatattggcctttgcatttggcctgcagtactatggcaaaaaaaacaagtccactgagtcagaaaattga

Cb5-C3:

atggcctcaaatcccaaaactttgaccttgaggaggtagctaagcacaacaacaaaaaggattgctggattattatcaatggaaagg
tgtatgatatcacaccattttggatgagcatccaggaggtgatgaagttttgctgacgtcaacagggaaggatgccaccattgattttga
agatgtggccacagtgattctgctatagaaatgatggaaaaatacttcattgggaaggttgacacttccactcttccacccaaagttag
ccatagtctgccacaacctacacaaacacatggcgctggcaatcaatcttctggatttgttgtaaagatcttgcaattcctgttgccattgtt
gatactgggcctcgcatttgccctgcagtattatggccaaaagaagcatgctagcacctcatga

Cb5-E1:

atgggtggggagcggaacaaggtcttctctttggccgaggtctctcagcacaacaatgccaaagactgttggcttgtcattcatggcaa
ggtttataatgtgacaaagttcttggaggaccaccctggaggggatgaggtcctgttgtcttccacagggaaagatgcaaccaatgattt
tgaggatattggtcacagcaccagcgccgtagccatgatggatgagttctatgttggagacattgatacatcaaccatcccagcaag
gttaagtacactcctccaaaacaacctcactataaccaggacaagatgccggagttcatcatcaggatcctccagtttctagttcccttgt
ttatcttgggtttggcagttggtattcgtttctacaccaaatcaacataa

atgtcttcagatcggaaggttctaagtttttgaagaagtttcaaagcacaacaaaactaaggattgttggcttattatttccggcaaggtgta
tgatgtgactccattcatggatgatcatcctggaggcgatgaagtcttgttgtcctcaacagggaaagatgctacaaatgatttttgaagac
gttggtcacagcgacactgcaagggacatgatggacaaatatttcattggtgagattgattcgtctagtgttccagcaactaggacatac
gttgcaccacagcaaccagcctacaaaccaagacaagacaccagaattcattatcaagattcttcagttccttgttccgatcttgatcttgg
gattggctcttgtcgtccgtcactataccaagaaagactag

Cb5-B:

atgggcggagacggaaaagttttcaccttgtccgaggttctcagcacagtagcgccaaggattgttggatcgtcatcgacggcaagg
tttatgatgtgacaaagttcttggatgatcatcctggtggtgatgaggttatcttgacttctacagggaaagatgcgaccgatgattcgag
gatgtgggacatagttcgactgcgaaagccatgctagatgagtactatgtgggtgatattgacacagctactgtgccggttaaagctaa
gtttgtgcctcctacgtcgacgaaagccgtggctactcaggataagagctcggattttgttattaagctccttcagttccttgttccacttcta
atcttaggcttggctttcggcattcggtactacactaagaccaaggctccttcttcttga

Cb5-C:

atggcgaatctaatttcgtttcacgatgtggctaaacataagtgcaagaacgattgttggattctcatccatggaaaggtctatgacatca
gcactttcatggacgaacatcccggaggtgacaatgttctcctcgccgtcaccgggaaagacgcgtcgatcgatttcgaagatgtgaa
ccatagcaaagatgccaaggagctaatgaagaaatactgtatcggtgacgttgaccagtcaacggttccggtgacgcaacagtatat
tccgccgtgggagaaggaatctacggcggcggaaacaactaaagaagaatctggaaagaagctgcttatctacttaattcctctcttg
atactcggcgttgctttcgctctcagattctacaacaacaagtag

Cb5-E:

atgggagacgaagcaaagatcttcactctttcagaagtttcagagcataatcaagctcatgactgttggattgtcatcaatggaaaggtg
tacaatgtgaccaagttcttgaagaccatccaggtggggacgatgttctcttgtcttcaacaggtaaggatgcaacggatgattttgagg
acgtgggtcacagcgagagtgcaagagaaatgatggagcagtactacgtaggagagattgatccaacaacaataccaaagaaa
gtcaaatacacacctcctaaacagcctcactacaatcaagacaagacctctgaattcataatcaagctcctccagttcctcgtaccccctt
gccattcttggtttagcagtcggaatccgtatctacaccaaatcagggtag

FIG. 11

ACL1:atgtctgccaacgagaacatctcccgattcgacgccctgtgggcaaggagcaccccgcctacgagctcttccataaccac
acacgatctttcgtctatggtctccagcctcgagcctgccagggtatgctggacttcgacttcatctgtaagcgagagaacccctccgtg
gccggtgtcatctatcccttcggcggccagttcgtcaccaagatgtactggggcaccaaggagactcttctccctgtctaccagcaggtc
gagaaggccgctgccaagcaccccgaggtcgatgtcgtggtcaactttgcctcctctcgatccgtctactcctctaccatggagctgctc
gagtaccccagttccgaaccatcgccattattgccgagggtgtccccgagcgacgagcccgagagatcctccacaaggcccaga
agaagggtgtgaccatcattggtcccgctaccgtcggaggtatcaagcccggttgcttcaaggttggaaacaccggaggtatgatgg
acaacattgtcgcctccaagctctaccgaccggctccgttgcctacgtctccaagtccggaggaatgtccaacgagctgaacaacat
tatctctcacaccaccgacggtgtctacgagggtattgctattggtggtgaccgatacccctggtactaccttcattgaccatatcctgcgat
acgaggccgaccccaagtgtaagatcatcgtcctccttggtgaggttggtggtgttgaggagtaccgagtcatcgaggctgttaagaa
cggccagatcaagaagcccatcgtcgcttgggccattggtacttgtgcctccatgttcaagactgaggttcagttcggccacgccggct
ccatggccaactccgacctggagactgccaaggctaagaacgccgccatgaagtctgctggcttctacgtccccgataccttcgagg
acatgcccgaggtccttgccgagctctacgagaagatggtcgccaagggcgagctgtctcgaatctctgagcctgaggtccccaaga
tccccattgactactcttgggccaggagcttggtcttatccgaaagcccgctgctttcatctccactatttccgatgaccgaggccagga
gcttctgtacgctggcatgcccatttccgaggttttcaaggaggacattggtatcggcggtgtcatgtctctgctgtggttccgacgacgac
tccccgactacgcctccaagtttcttgagatggttctcatgcttactgctgaccacggtcccgccgtatccggtgccatgaacaccattatc
accaccgagctggtaaggatctcattcttccctggttgctggtctcctgaccattggtacccgattcggaggtgctcttgacggtgctgc
caccgagttcaccactgcctacgacaagggtctgtccccccgacagttcgttgataccatgcgaaagcagaacaagctgattcctggt
attggccatcgagtcaagtctcgaaacaaccccgatttccgagtcgagcttgtcaaggactttgttaagaagaacttcccctccaccca
gctgctcgactacgcccttgctgtcgaggaggtcaccacctccaagaaggacaacctgattctgaacgttgacggtgctattgctgttct
tttgtcgatctcatgcgatcttcggtgccttactgtggaggagactgaggactacctcaagaacggtgttctcaacggtctgttcgttctc
ggtcgatccattggtctcattgcccaccatctcgatcagaagcgactcaagaccggtctgtaccgacatccttgggacgatatcaccta
cctggttggccaggaggctatccagaagaagcgagtcgagatcagcgccggcgacgtttccaaggccaagactcgatcatag ACL2:atgtcagcgaaatccattcacgaggccgacggcaaggccctgctcgcacactttctgtccaaggcgcccgtgtgggccga
gcagcagcccatcaacacgtttgaaatgggcacacccaagctggcgtctctgacgttcgaggacggcgtggcccccgagcagatct
tcgccgccgctgaaaagacctacccctggctgctggagtccggcgccaagtttgtggccaagcccgaccagctcatcaagcgacga
ggcaaggccgcctgctggcactcaacaagtcgtgggaggagtgcaagccctggatcgccgagcgggccgccaagcccatcaa
cgtggagggcattgacggagtgctgcgaacgttcctggtcgagcccttgtccccacgaccagaagcacgagtactacatcaacat
ccactccgtgcgagagggcgactggatcctcttctaccacgagggaggagtcgacgtcggcgacgtggacgccaaggccgccaa
gatcctcatccccgttgacattgagaacgagtacccctccaacgccacgctcaccaaggagctgctggcacacgtgcccgaggacc
agcaccagaccctgctcgacttcatcaaccggctctacgccgtctacgtcgatctgcagtttacgtatcggagatcaacccctggtcg
tgatccccaccgcccagggcgtcgaggtccactacctggatcttgccggcaagctcgaccagaccgcagagtttgagtgcggcccc
aagtgggctgctgcgcgggtccccgccgctctgggccaggtcgtcaccattgacgccggctccaccaaggtgtccatcgacgccgg
ccccgccatggtcttcccgctcctttcggtcgagagctgtccaaggaggaggcgtacattcggagctcgattccaagaccggagct
tctctgaagctgactgttctcaacgccaagggccgaatctggaccttgtggctggtggaggagcctccgtcgtctacgccgacgccat
tgcgtctgccggctttgctgacgagctcgccaactacggcgagtactctggcgctcccaacgagacccagacctacgagtacgccaa
aaccgtactggatctcatgacccggggcgacgctcaccccgagggcaaggtactgttcattggcggaggtatcgccaacttcaccca
ggttggatccaccttcaagggcatcatccgggccttccgggactaccagtcttctctgcacaaccacaaggtgaagatttacgtgcgac
gaggcggtcccaactggcaggagggtctgcggttgatcaagtcggctggcgacgagctgaatctgcccatggagatttacggcccc
gacatgcacgtgtcgggtattgttccttttggctctgcttggaaaagcggcccaagaatgtcaagccttttggcaccggaccttctactgagg
cttccactcctctcggagtttaa

FIG. 12

PLANT GENES ASSOCIATED WITH SEED OIL CONTENT AND METHODS OF THEIR USE

RELATED APPLICATIONS

This application claims benefit of priority to U.S. Provisional Patent Application Ser. Nos. 61/287,572, filed Dec. 17, 2009, and 61/328,545, filed Apr. 27, 2010, the contents of which are herein incorporated by reference into this application.

SEQUENCE LISTING

This application is accompanied by a sequence listing that accurately reproduces the sequences described herein.

BACKGROUND

1. Field of the Invention

The present disclosure relates to certain plant genes implicated in oil production and the use of such genes to boost or to modulate oil content in plant seeds. More particularly, the present disclosure relates to modulation of the ratio between different fatty acids in a plant or parts thereof through controlled expression of these genes.

2. Description of the Related Art

Plant oils are used in a variety of applications. Plants that synthesize and store large amounts of oils in their seeds are an important source of oils for both human and animal consumption. Plant oils are also widely used in various industries, such as in the paint and coating industry. Depending upon the intended use, different fatty acid compositions in plant oils are desired.

Plant and animal oils (or fats) are composed almost entirely of triacylglycerols (TAGs). TAG is an ester formed by fatty acids and glycerol where the fatty acids are esterified to the three hydroxyl groups of glycerol. Plant and fish fat sources are generally considered more healthy than fat sources from most animals because these plant and fish fat sources typically have higher content of unsaturated fatty acids. The intake amount of unsaturated fatty acids and the ratio between these fatty acids in the food sources have certain causal relationship with the incidence of cardiovascular and other chronic diseases in humans. For review, see Simopoulos, A P, Exp Biol Med (Maywood), 233(6):674-88 (2008). Moreover, saturated fatty acids typically have higher melting points than unsaturated fatty acids and are thus less desirable in many applications. For instance, when used as a fuel, saturated fatty acids may cause clouding at low temperatures, and may confer poor cold flow properties to the fuel.

Long chain polyunsaturated fatty acids are essential components of phospholipids in the cell membrane and are also precursors of various metabolites which are important in various functions of the human body. Certain long chain polyunsaturated fatty acids can be synthesized in humans by the "omega-6 pathway" from dietary omega-6 and omega-3 fatty acids, e.g., linoleic acid (also referred to as LA or 18:2) and α-linolenic acid (also referred to as ALA or 18:3), respectively. However, because humans cannot synthesize LA or ALA, these fatty acids have to be obtained from diet or other sources.

Because omega-6 and omega-3 fatty acids each play an important yet distinct role in the human body, it is important to maintain an optimal balance between these two types of unsaturated fatty acids. Although a ratio of 5:1 has been recommended for omega-6 and omega-3 fatty acids in human diet, the ratio has shifted heavily toward omega-6 fatty acids in the current western diet. Sargent, J. R. (1997) Br. J. Nutr. 78, Suppl. 1, 5-13. Indeed, the amount of omega-6 fatty acids is, by some estimates, up to 30-fold higher than the recommended value. This skewed ratio between omega-6 and omega-3 fatty acids is at least partially attributable to the consumption of increasing amount of vegetable oils and other foods that are rich in LA, but low in ALA. Simopoulos, A. P. (1999) Am. J. Clin. Nutr. 70, 560S-569S. Thus, increasing the amount of ALA in common food sources such as plant oils may help correct the skewed ratio between dietary omega-6 and omega-3 fatty acids.

TABLE 1

Characteristics of the major Fatty Acids

| Carbons: Double Bonds | Name | Saturation |
|---|---|---|
| 16:0 | Palmitic Acid | Saturated |
| 18:0 | Stearic Acid | Saturated |
| 18:1 | Oleic Acid | monounsaturated |
| 18:2 | Linoleic Acid | ω-6 polyunsaturated |
| 18:3 | α-Linolenic Acid | ω-3 polyunsaturated |

Table 1 summarizes major fatty acids in plants. The designations (18:1), (18:2), (18:3), etc., refer to the number of carbon atoms in the fatty acid chain and the number of double bonds therein. As commonly used in the field and in this disclosure, the designations sometimes take the place of the corresponding fatty acid common name. For example, oleic acid (18:1) contains 18 carbon atoms and 1 double bond, and may be referred to as "18:1".

In higher eukaryotes, cytochrome b5 (Cb5) is a small heme-binding protein typically associated with the endoplasmic reticulum (ER) and the outer mitochondrial membranes. Cb5 provides electrons in desaturation of acyl CoA fatty acids (FAs) [1]. In higher plants, Cb5 has also been implicated as electron donor in hydroxylation of acyl CoA FAs [2-4], divergent FAD2 such as conjugase, acetylenase mediated reactions [5-7], desaturation and hydroxylation of sphingolipids [8, 9], sterol desaturations [10] and cytochrome P450 reactions [11]. Apart from its role in lipid metabolism associated reactions, recently it has been reported that interaction of ER resident Cb5 with plasma membrane associated sucrose and sorbitol transporters results in up-regulation of their affinity to their substrate sugars which is critical for adjusting sugar level in cells [12].

Higher plants such as tobacco [16,17], *Arabidopsis* [4,18], *Tung* [19], *Crepis alpina* [7], and soybean are uniquely endowed with multiple Cb5 genes as opposed to a single one in mammals [20] and yeast [21], respectively. Apart from the typical ER or outer mitochondrial membrane associated "independent" Cb5, the Cb5 like domain has been reported in many front-end desaturases, such as $\Delta^5$ or $\Delta^6$ desaturase of mammals and *C. elegans* [8] and $\Delta^6$-desaturase of borage plants [22]. The Cb5 motif has also been reported in higher plant sphingolipid $\Delta^8$-LCB desaturase [8] and nitrate reductase [23]. The extensive molecular-genetic and biochemical characterization of higher plant FAD2 and FAD3 in the past has led to significant advances in our understanding of 18C PUFAs synthesis; however, parallel information regarding relationship of various Cb5 isoforms in such desaturases is limited.

SUMMARY

The instrumentalities described herein overcome the problems outlined above and advance the art by providing genes that may play an important role in regulating seed oil content. More particularly, the Cb5 gene products are known to play a role in fatty acid desaturation. The present disclosure provides the first report that co-expression of a non-fungal FAD3 desaturase and certain Cb5 genes in yeast leads to increased production of omega-3 fatty acids. The present disclosure also reports the different functionalities of different Cb5 genes from higher plant and offers a method to modulate poly-unsaturated fatty acid (PUFA) levels in plants.

According to the present disclosure, plants may be genetically modified to produce higher levels of oil in the seeds. In one aspect, plants may be genetically modified such that the ratio between different fatty acids may be altered based on different needs. For instance, the levels of unsaturated fatty acids, such as 18:3, may be rendered higher than those in the unmodified plants. Such plants with higher unsaturated fatty acids may have higher nutritional value due to the multiple benefits of unsaturated fatty acids in the diet. Moreover, such plants with higher unsaturated fatty acids may also have industrial application in paint and coating industries because of the quick drying properties of the unsaturated fatty acids.

In one embodiment, different Cb5 genes from soybean (*Glycine max* var. Williams) or *Arabidopsis* are characterized by using a mutant yeast strain deficient in its endogenous Cb5 gene. Yeast has proven to be an excellent experimental system for functional characterization of plant lipid biosynthetic genes such as desaturases [24-27], conjugases [5], epoxygenases [28], hydroxylases [3, 29], Cb5 [19] and NADH: cytochrome 115 reductase [4, 30]. Different Cb5 isoforms of *Arabidopsis* are not equally efficient in ω-6 desaturation. This observation is in contrast to the relatively similar efficiencies displayed by soybean Cb5 isoforms. With regard to ω-3 desaturation, certain Cb5 isoforms of both soybean and *Arabidopsis* are able to accumulate significantly more 18:3 than others under comparable growth conditions. These differences in ω-3 desaturation efficiencies have been further confirmed by their co-expression with non-native FAD3

In another embodiment, it is disclosed that Cb5 isoforms from plants such as soybean or *Arabidopsis* are capable of modulating omega-3 desaturation in yeast. In most angiosperms, FAD3 is the primary desaturase responsible for the production of omega-3 FA, such as α-linolenic Acid (18:3). The roles of various Cb5 isoforms in omega-3 desaturation and their interaction with FAD3 are investigated in a yeast system. The results obtained in this study suggest that not all Cb5 isoforms from *Arabidopsis* and soybean are equally efficient in omega-3 desaturation, as evidenced by significant variation in α-linolenic acid (ALA, 18:3) accumulation when different Cb5 isoforms are expressed in the yeast system. Under comparable growth conditions, certain Cb5 isoforms from *Arabidopsis* or soybean have greater efficiency than others in producing and accumulating 18:3.

The important roles played by various Cb5 isoforms are confirmed by analyses in which *Arabidopsis* Cb5 genes are replaced by soybean Cb5 genes or vice versa. It is further disclosed that the efficiency of omega-3 desaturation is determined not only by the nature of Cb5 but also by the efficiency of the respective desaturase as well as the interplay between Cb5 and FAD3. Notably, with co-expression of soybeans Cb5 genes and native FAD3, more than 2 fold increase in 18:3 production are observed in mutant cb5 yeast as compared to those expressing FAD3 alone. Variation of functionalities among different Cb5 isoforms with respect to their 18:3 levels are also shown. The 18:3 levels when Cb5-C2 or Cb5-E1 is expressed are about 1.5 fold more than Cb5-C3. When Cb5-A1 is expressed, the 18:3 levels are lower than those of Cb5-C2 & Cb5-E1 but greater than the 18:3 levels when Cb5-C3 is expressed.

The level of 18:3 in soybean seeds is about 8% of total seed fatty acids. It has been shown that overexpression of FAD3 gene could help increase the percentage of 18:3 to about 50% (Cahoon 2003), or in one case even up to about 70% (Damude et al, 2006) of total seed fatty acids. However, the extraction of these fatty acids is not commercially feasible because the levels of the fatty acids are still too low. Further increase in desaturation through overexpression of FAD3 may be limited due to the limited availability of other co-factors. Cb5 may be one of such co-factors. Co-overexpression of certain FAD3 and certain Cb5 isoforms in a transgenic plant may help increase the 18:3 content to greater than 70% of the total fatty acids (w/w), preferably to 80% (w/w).

As disclosed herein, different Cb5 isoforms have different functionalities. Certain Cb5 isoform may work more efficiently with certain FAD3 proteins to facilitate fatty acid desaturation, but less efficiently with other desaturases. In one aspect, certain Cb5 genes may be overexpressed with a suitable FAD3 gene in a seed specific manner. Such co-expression of the Cb5-FAD3 genes may potentially increase 18:3 significantly to a level such that it would be commercially viable to extract 18:3 from the seeds. In another aspect, the trait of higher overall oil content may be combined with another trait with higher levels of a specific fatty acid. For instance, the high seed oil trait may be combined with the high 18:3 trait to produce soybean crops with greater premium than the average unmodified soybean plants.

The disclosed genes that are associated with seed oil and fatty acid modulation include but are not limited to genes encoding enzymes, scaffolding proteins, electron donors, electron acceptors, electron carriers, which play a role in the fatty acid pathways. These genes, including but not limited to the Cb5 genes or desaturase genes, may be introduced into a host plant to generate a genetically modified plant that produces higher seed oil content or have more desirable fatty acid ratio in the seed oil. Alternatively, the endogenous Cb5 and/or desaturase genes of a plant may be modified such that these genes will be expressed at elevated levels as compared to the unmodified genes. The Cb5 genes or desaturase genes to be introduced into a host plant may be isolated or derived from said host plant or from a different strain or species. For instance, a fungal gene may be introduced into a plant, or vice versa.

In another aspect, the disclosed method may be practiced as follows: In step one, one or more plants are created comprising one or more transgenes that enhance the expression of an endogenous FAD3 gene. In step two, at least one seed is obtained from each of said one or more plants created in step one. Step three may be performed to determine the total seed oil content and the percentage by weight of linolenic acid in the total fatty acids using the seed obtained from step two. Step four may then be performed to identify a plant that yields seeds having a linolenic acid content of more than about 10%, 20%, 30%, 40%, 50%, 60%, 70%, or more preferably 80% of total seed fatty acids by weight.

In another aspect, the disclosed method may be practiced as follows: in step one, one or more plants are created comprising one or more transgenes that enhance desaturation of fatty acids to produce linolenic acids. In step two, at least one seed is obtained from each of said one or more plants created in step one. Step three may be performed to determine the total seed oil content and the percentage by weight of linolenic acid in the total fatty acids using the seed obtained from step two. Step four may be performed to identify a plant that yields seeds having a linolenic acid content of more than about 10%, 20%, 30%, 40%, 50%, 60%, 70%, or more preferably 80% of total seed fatty acids by weight. The transgenes in step one may be isolated from the host plant, or they may be isolated from a heterologous source, such as a different plant, fungus, etc. In a preferred embodiment, the transgenes include two genes, one encoding FAD3, the other encoding a Cb5 isoform. In another aspect, the one or more transgenes are placed under control of a tissue specific promoter such that the transgenes are expressed in a seed specific manner.

According to one aspect of this disclosure, a transgene may be introduced into a host organism for generating a transgenic organism in order to enhance the quantity and/or quality of oil produced by the host organism. The method of include the step of introducing a first transgene into a host organism wherein the first transgene has a sequence that is at least 95%, preferably 99%, more preferably 100%, identical to one of the polynucleotides of SEQ ID. Nos. 1-8. Preferably, the first transgene encodess a polypeptide which has an amino acid sequence that is at least 95%, preferably 99%, more preferably 100%, to the sequence of the polypeptide encoded by one of the polynucleotides of SEQ ID. Nos. 1-8. In yet another aspect, the transgene may be a citrate lyase that catabolize citrates. For example, the ACL1 gene, ACL2 gene, or both, can be introduced into a host plant, whose overproduction in the plastids may help boost the synthesis of acetyl CoA. In another aspect, the transgene can have least 95% sequence identity with one of the polynucleotides of SEQ ID. Nos. 9-10.

The method may further include a step of allowing said host organism to express a protein encoded by the first transgene. The host organism is preferably a plant and the transgenic organism is preferably a transgenic plant. In addition to the first transgene, the method may include a step of introducing a second transgene into said host plant, wherein the second transgene encodes a fatty acid desaturase, such as FAD2 or FAD3 of higher plant. In one aspect, the first and second transgenes are from the same plant species. In another aspect, the first and second transgenes are from different plant species.

In one aspect, the transgenic plant produces higher oil content than the non-transgenic host plant. In another aspect, the transgenic plant produces oil that has higher percentage of unsaturated fatty acids than the fatty acids produced by the non-transgenic host plant. The disclosed method may be applicable to any plant, and preferably to oil plant, such as soybean, *arabidopsis*, corn, peanut and canola, among others.

Conventional breeding may also be used to generate plant lines with the desirable oil content or desired ratio between different fatty acids. Lines that naturally express relatively high levels of Cb5 and/or FADs may be used as parental strains for breeding in order to generate new lines that express relatively high levels of both Cb5 and FAD.

In another embodiment, the *Yarrowia* ATP-citrate lyase (ACL) genes, such as ACL1 (Genbank: XM_504787) and ACL2 (Genhank:XM_503231), may be introduced into a host plant to generate transgenic plant that produce higher levels of seed oil content as compared to the non-transgenic host plant. To direct the ACL gene products to the plastids, the genes may be engineered to contain a plastid localization sequence. Because ACL enzymes can catabolize available citrates inside the plastids, overproduction of ACL enzymes in the plastids may help boost the synthesis of acetyl CoA. The increased acetyl CoA, in turn, may lead to increased synthesis of fatty acids and enhanced oil accumulation in the seeds.

Various forms of the genes disclosed herein may be used which may not be 100% identical to the disclosed genes. Such altered genes may encode proteins that are capable of performing substantially the same or similar functions as those performed by the proteins disclosed herein. By way of example, mutated FAD3 genes encoding FAD3 proteins having at least 70%, 80%, 90%, 95%, 98%, 99%, or 100% identity with the FAD3 sequences disclosed herein may be used. These FAD3 genes include but are not limited to the soybean and *Arabidopsis* FAD3 genes disclosed here. Similarly, mutated Cb5 isoforms or fungal ACL genes may be used. Indeed, certain mutations, either by point mutation, truncation or insertion, may confer upon the expressed proteins certain desirable property, such as localization signal, binding motif, etc.

In another aspect, the ACL genes, Cb5 genes and various genes encoding desaturases may be co-expressed in the same plant to achieve both higher oil content and desirable ratio between specific fatty acids, such as, for example, higher percentage of unsaturated fatty acids by weight of the total fatty acids.

BRIEF DESCRIPTION OF THE DRAWINGS

FIG. 8 shows alignment of the deduced amino acid sequence of soybean Cb5 (GmCb5) isoforms with known and putative ER targeted Cb5 proteins of Tung and *Arabidopsis* using vector NTI software.

FIG. 10 shows the nucleic acid sequences of Soybean (*Glycine max*) cytochrome b5 (Cb5) genes, Cb5A1 (SEQ ID. No. 1), Cb5-C2 (SEQ ID. No. 2), Cb5-C3 (SEQ ID. No. 3), Cb5-E1 (SEQ ID. No. 4).

FIG. 11 shows the nucleic acid sequences of *Arabidopsis* (*Arabidopsis thaliana*) cytochrome b5 (Cb5) genes, Cb5-A (SEQ ID. No. 5), Cb5-B (SEQ ID. No. 6), Cb5-C (SEQ ID. No. 7), Cb5-E (SEQ ID. No. 8).

FIG. 12 shows the nucleic acid sequences of *Yarrowia lipolytica* ACL1 (SEQ ID. No. 9) and ACL2 (SEQ ID. No. 10) genes.

DETAILED DESCRIPTION

Figure 1:
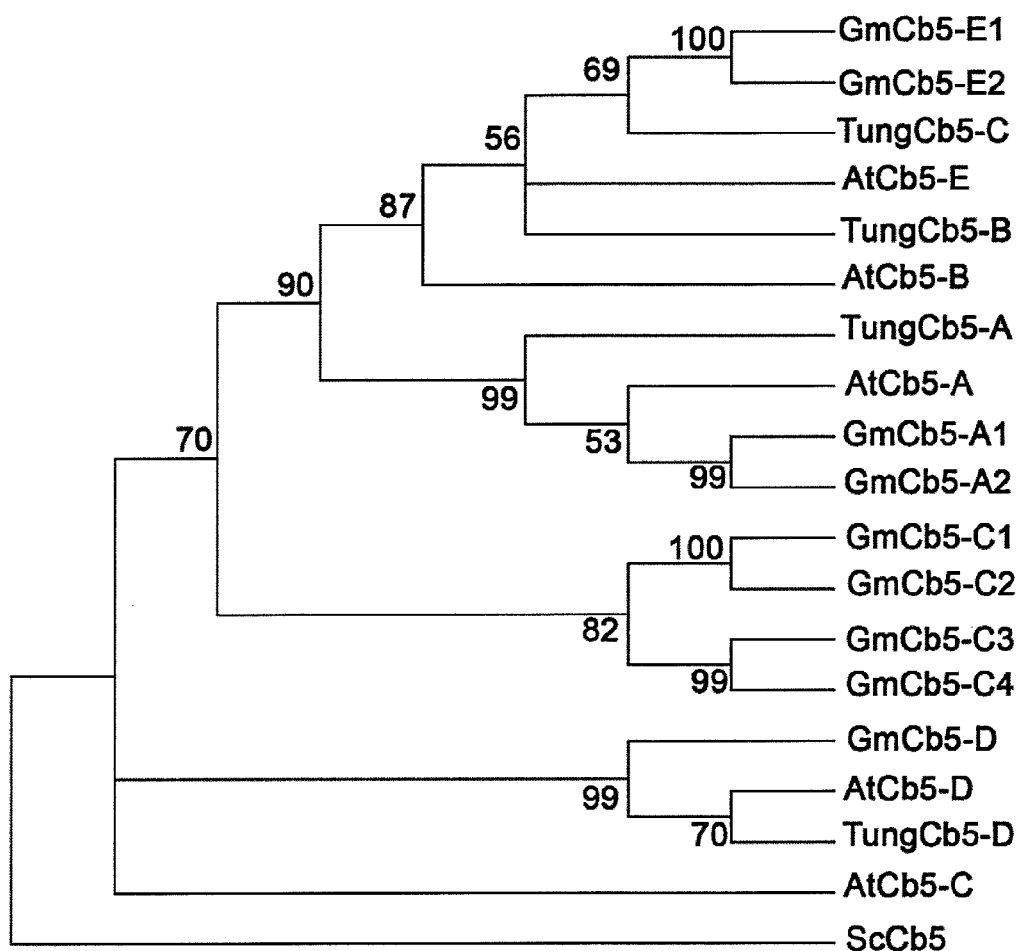
FIG. 1 illustrates the phylogenetic relationship of soybean (*Glycine max*) Cb5 proteins.

Plants synthesize fatty acids via a common metabolic pathway known as the fatty acid synthetase (FAS) pathway. Beta-ketoacyl-ACP (acyl carrier protein moiety) synthases are important rate-limiting enzymes in the fatty acid synthetase pathway. Beta-ketoacyl-ACP synthases exist in several versions in plant cells. Beta-ketoacyl-ACP synthase I catalyzes chain elongation to palmitoyl-ACP (C16:0), whereas beta-ketoacyl-ACP synthase II catalyzes chain elongation to stearoyl-ACP (C18:0). Beta-ketoacyl-ACP synthase IV is a variant of beta-ketoacyl-ACP synthase II, and can also catalyze chain elongation to 18:0-ACP. In soybeans, the major products of FAS are 16:0-ACP and 18:0-ACP. Desaturation of 18:0-ACP to form 18:1-ACP in soybean and many other plants is catalyzed by a soluble delta-9 desaturase (also referred to as "stearoyl-ACP desaturase") located in the plastids.

The products of the plastidial FAS and delta-9 desaturase, namely, 16:0-ACP, 18:0-ACP, and 18:1-ACP, may be hydrolyzed by specific thioesterases. Plant thioesterases can be classified into two families based on sequence homology and substrate preference. The first family, FATA, includes long chain acyl-ACP thioesterases having activity primarily on 18:1-ACP. Enzymes of the second family, FATB, commonly utilize 16:0-ACP (palmitoyl-ACP), 18:0-ACP (stearoyl-ACP), and 18:1-ACP (oleoyl-ACP). These thioesterases play an important role in determining chain length during de novo fatty acid biosynthesis in plants, and are thus useful in the provision of various modifications of fatty acyl compositions, particularly with respect to the relative proportions of various fatty acyl groups that are present in seed storage oils.

The products of the FATA and FATB reactions, i.e., the free fatty acids, leave the plastids and are converted to their respective acyl-CoA esters. Acyl-CoAs are substrates for the lipid-biosynthesis pathway (Kennedy Pathway), which takes place in the endoplasmic reticulum (ER) of plant cells. This pathway is responsible for membrane lipid formation as well as the biosynthesis of triacylglycerols, which are the primary constituent of the seed oil. Additional membrane-bound desaturases in the ER may further desaturate 18:1 to polyunsaturated fatty acids, such as 18:2 and 18:3.

The soybean genome possesses two seed-specific isoforms of a delta-12 desaturase FAD2, designated FAD2-1A and FAD2-1B, which differ from each other in only 24 amino acid residues. The genes encoding FAD2-1A and FAD2-1B are designated Glyma10g42470 on Linkage Group 0 and Glyma20g24530 on Linkage Group I on the soybean genome sequence, respectively (Glyma1.0, Soybean Genome Project, DoE Joint Genome Institute). FAD2-1A and FAD2-1B are found in the ER where they can further desaturate oleic acid to polyunsaturated fatty acids. The delta-12 desaturase catalyzes the insertion of a double bond into oleic acid (18:1), forming linoleic acid (18:2) which results in a consequent reduction of oleic acid levels. A delta-15 desaturase (FAD3) catalyzes the insertion of a double bond into linoleic acid (18:2), forming linolenic acid (18:3). The soybean genome possesses four isoforms of the FAD3 genes, such as FAD3-1A (Anai et al., 2005) and FAD3B (Bilyeu et al., 2003), among others.

In higher plants, de novo synthesis of FAs takes place exclusively in plastids but their subsequent desaturation occurs in two different compartments, i.e. plastids and ER. Besides oxygen, certain co-factors are required for the introduction of double bonds in fatty acids. These co-factors may help provide electrons to the respective desaturases housed in these two compartments. In the plastids, the light reaction generated reduced ferredoxin serves as co-factor. In the ER, the Cb5 protein donates electrons to both FAD2 and FAD3 [13]. Although the relative contribution of two pathways towards the final products of desaturation varies with tissues and species, in majority of angiosperms synthesis of most PUFAs passes through ER resident FAD2 (18:1 to 18:2 desaturation) and FAD3 (18:2 to 18:3 desaturation) desaturases [14, 15].

In higher plants, almost all the fatty acids are synthesized from acetyl CoA. It has been shown that elevation of the amount of acetate in plastids by constitutive expression of rat ATP citrate lyase (ACL) in *Arabidopsis* enhances the production of fatty acids in the leaves of transgenic *Arabidopsis*. See Rangasamy and Ratledge (2000).

According to the present disclosure, the different Cb5 isoforms of different higher plants may not have the same desaturation efficiencies. The display of higher ω-6 desaturation by Cb5-C & Cb5-B and higher ω-3 desaturation by Cb5-B & Cb5-E isoforms of *Arabidopsis* indicate that they may interact with different efficiencies with FAD2 and FAD3, respectively. In contrast to *Arabidopsis*, the Cb5 isoforms of soybean do not exhibit differential ω-6 desaturation. However, different soybean Cb5 isoforms exhibit different ω-3 desaturation efficiencies. Moreover, the results obtained in this study further suggest that final product outcome of ω-3 or ω-6 desaturation is determined not only by the nature of Cb5 but also by the properties of the fatty acid desaturases.

Two electron transport chains exist in the ER: one is the NADPH: cytochrome P450 reductase & P450s, and the other is the NADH:cytochrome b5 reductase & Cb5 [18]. The latter has been implicated as major route for providing reducing equivalents to ER based FAD2 (18:1 to 18:2 desaturation) and FAD3 (18:2 to 18:3 desaturation) desaturases [14, 15]. Biochemical evidence also indicates that both FAD2 and FAD3 of higher plants utilize Cb5 as an electron donor [41]. Despite wealth of data showing regulation of 18C PUFA synthesis by higher plant FAD2 and FAD3, the parallel information regarding role of various Cb5 isoforms in such desaturase mediated reactions are limited. Here, the contribution of various Cb5 isoforms from either *Arabidopsis* or soybean in FAD2 and FAD3 mediated reactions is demonstrated by using a mutant yeast strain deficient in endogenous Cb5 gene.

Figure 2:
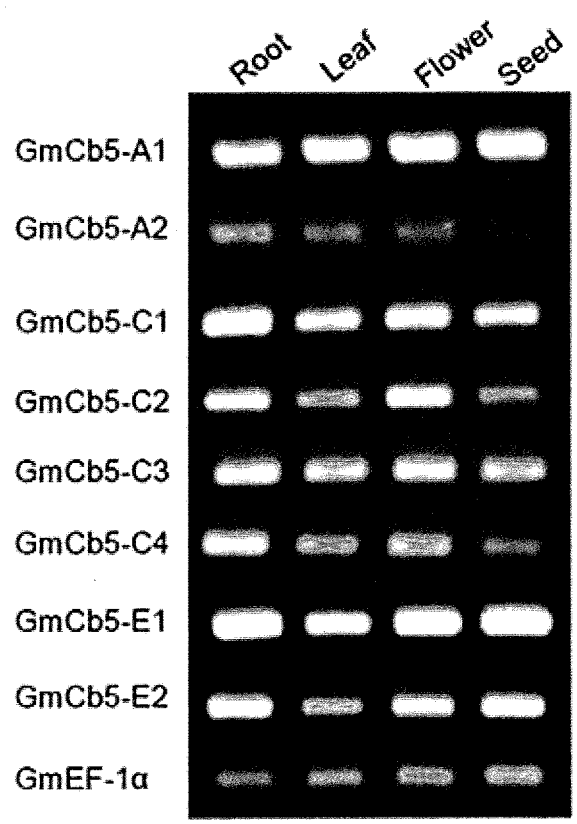
FIG. 2 shows the organ specific Cb5 gene expression analyses of soybean (*Glycine max* var. Williams).

Like *Arabidopsis*, the Cb5 isoforms of soybean were similarly diverged, as demonstrated by the phytogenetic tree of FIG. 1. The expression pattern of these soybean Cb5 genes are studied. Notably, despite constitutive pattern of expression displayed by all GmCb5 genes, the expression of GmCb5-A1 and GmCb5-E1 were higher than others in all the organs including seed, which is the site of oil storage and TAG synthesis (FIG. 2).

Interestingly, these different soybean Cb5 proteins display similar ω-6 desaturation efficiencies. Although such results are consistent to those observed with Cb5 isoforms of Tung (19), soybean FAD2 typically results in about 10 fold higher di-unsaturated FAs accumulation in mutant cb5 yeast as compared to *Arabidopsis* FAD2 even though the availability of precursors is similar. These results suggest much higher interaction efficiency of soybean FAD2 with functional Cb5 domain of stearoyl CoA desaturase [35]. This proposition is also supported by demonstration of relatively similar level of total di-unsaturated FAs in mutant cb5 yeast expressing either FAD2 alone or co-expressing Cb5 and FAD2 particularly at lower temperature conditions (FIG. 3A). Taken together, these data suggest that the apparent lack of discrimination among soybean Cb5 isoforms in 0-6 desaturation may be due to additional contribution by functional Cb5 domain of stearoyl CoA desaturase. It is disclosed here experiments exploring the role of soybean Cb5 isoforms in ω-6 desaturation by using yeast ole1 cb5 double mutant, which is deficient in stearoyl CoA desaturase and microsomal Cb5 respectively.

Yeast is a convenient system to study FA desaturation as it provides a eukaryotic ER, Cb5, and NADH: cytochrome b5 reductase. It has been shown that several factors associated with yeast metabolism, such as the rate of FAs synthesis, the rate of their breakdown, and the rate of exogenous FAs incorporation, determine the level of the final product accumulation. However, existing data are only semi-quantitative, at best [25]. The results disclosed herein demonstrate that different Cb5 isoforms of *Arabidopsis* are not similarly efficient in ω-6 desaturation, as evidenced by display of ~1, 5-2 fold higher di-unsaturated FAs (18:2 and 16:2) by both Cb5-B and Cb5-C than others at higher (FIG. 4A) or lower temperature (FIG. 4B), respectively. By contrast, in the ease of soybean Cb5 isoforms, the differences in their total di-unsaturated FAs level at either higher (FIG. 3A) or lower (FIG. 3B) temperature are not significant, which suggests that different isoforms have similar ω-6 desaturation efficiencies. It is interesting to note that soybean and *Arabidopsis* experiments were performed independently but at comparable growth conditions. More particularly, FAD2 precursors (18:1 and 16:1) were similarly available in both the soybean and *Arabidopsis* experiments, which rules out the possibility of any discrimination that might have contributed to the different results from soybean and *Arabidopsis*. Although the transcript levels have not been measured, differential transcript accumulation at comparable growth conditions is not likely to be a factor, as FAD2 and Cb5 of both soybean and *Arabidopsis* were driven by the same GAL10 and GAL1 promoters, respectively.

In addition to the differences in behavior of Cb5 isoforms ω-6 desaturation, the Cb5 isoforms of soybean and *Arabidopsis* also demonstrate significant variation in ω-3 desaturation at comparable growth conditions. The soybean Cb5-C2, Cb5-E1 & Cb5-A1 (FIG. 5A) and *Arabidopsis* Cb5-B & Cb5-E (FIG. 6A) consistently showed higher 18:3 accumulations compared to their other isoforms. The soybean (FIG. 5) and *Arabidopsis* (FIG. 6) experiments were performed independently but at comparable growth conditions as FAD3 precursor (18:2) were similarly available, which rules out its involvement in the observed differential 18:3 accumulation. More importantly, the higher 18:3 accumulation under comparable growth conditions by soybean Cb5-E1 (GmCb5-E1) & Cb5-A1 (GmCb5-A1) and *Arabidopsis* Cb5-B(AtCb5-B) & Cb5-E(AtCb5-E) even with non-native FAD3 (FIG. 7A) demonstrate retention of their higher ω-3 desaturation efficiency. Similar trend was also observed at lower temperature condition with most Cb5 isoforms except for AtCb5-C which shows 18:3 level that is similar to that of AtCb5-B (FIG. 7B).

Figure 5:
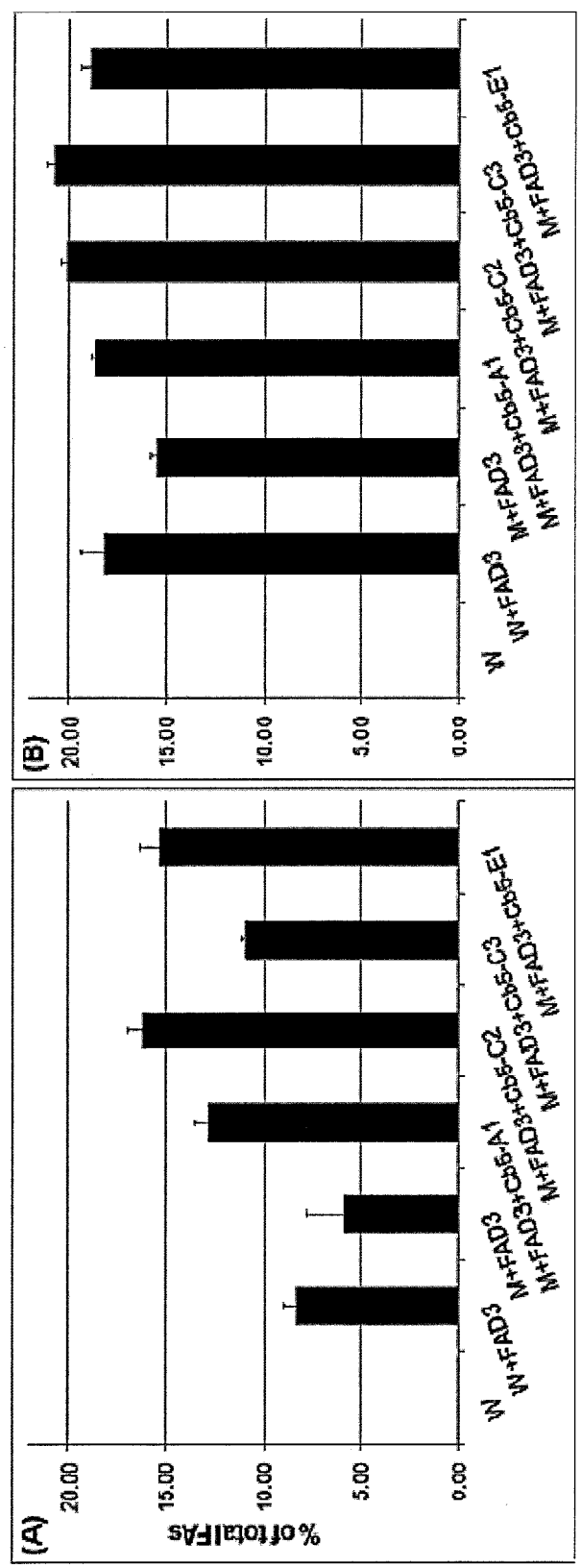
FIG. 5 shows the 18:3 content of yeast co-expressing Cb5 and FAD3 of soybean.
Figure 6:
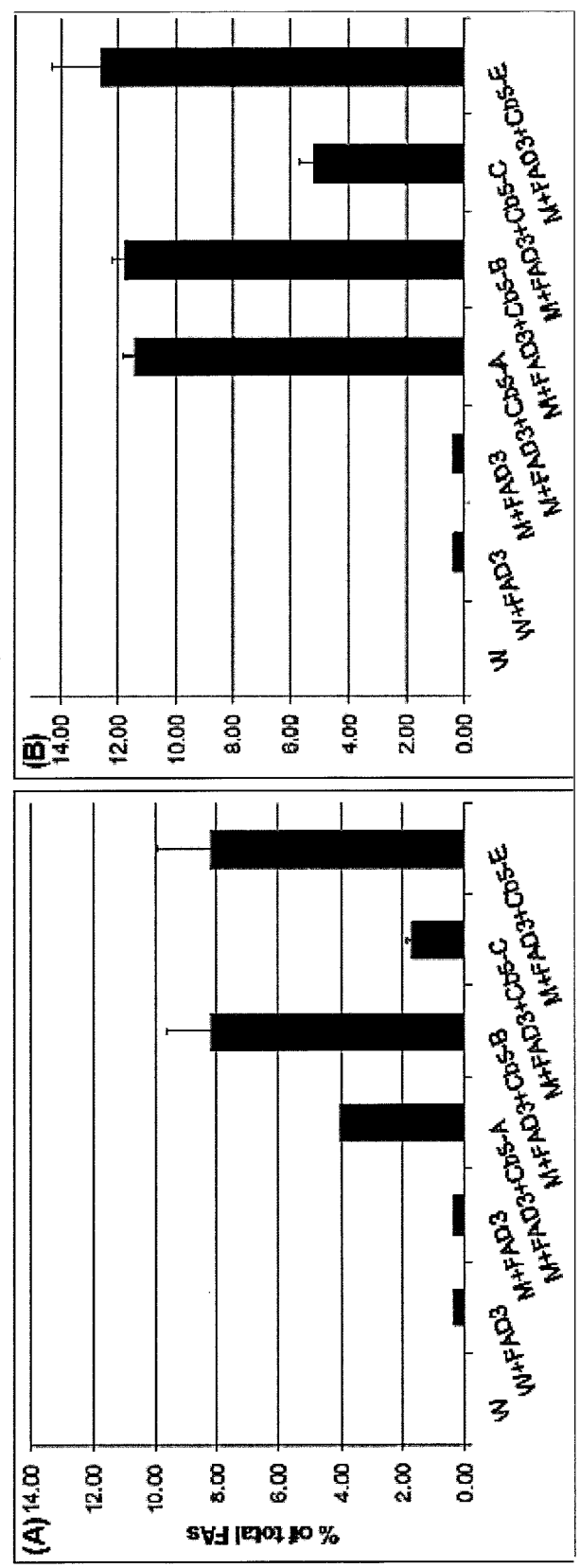
FIG. 6 shows the 18:3 content of yeast co-expressing Cb5 and FAD3 of *Arabidopsis*.

Although retention of differential ω-3 desaturation property was observed with most Cb5 isoforms of both soybean and *Arabidopsis*, a significant ~3 fold reduction in 18:3 level with both GmCb5-C2 & GmCb5-C3 particularly under condition with non-native AtFAD3 (FIG. 7) compared to the level achieved with their native FAD3 (FIG. 5) was intriguing. It is important to note that *Arabidopsis* Cb5-C accumulated 2-4 folds less 18:3 than others under condition of their co-expression with native FAD3, (FIG. 6). However, co-expression of *Arabidopsis* Cb5-C (AtCb5-C with non-native GmFAD3 resulted in significant 2 to 4 fold increase in 18:3 level at higher and lower temperature conditions (FIGS. 7A&B) compared to level it achieved during co-expression with native FAD3, (FIGS. 6A&B) respectively.

It is interesting that higher 18:3 accumulation with 'C' class of Cb5 proteins, whether from soybean or *Arabidopsis*, was observed only with soybean FAD3 and not with *Arabidopsis* FAD3. In phylogenetic analyses (FIG. 1), among four arbitrary classes of Cb5 proteins viz. A, B, C and E, the 'C' class from soybean formed a separate group that clustered close to *Arabidopsis* Cb5-C (AtCb5-C). The amino acids alignment of different Cb5 proteins from soybean, Tung and *Arabidopsis* indicated that despite significantly higher level of overall identity of 'C' class of proteins with other classes, there is considerable diversity at their C-termini (boxed), particularly in the region preceding the trans-membrane domain (FIG. 8). Whether such differences in amino acids are of any significance for greater interaction efficiency of 'C' class of Cb5 proteins with soybean FAD3 as opposed to *Arabidopsis* FAD3 is unclear, but the results presented herein indicate that evolutionary divergence in Cb5 isoforms might have contributed to their differential interaction efficiencies with desaturases as evidenced by variations in their desaturation products outcome. The demonstration of significantly higher product accumulations by the desaturases (FAD2/FAD3) of soybean as compared to *Arabidopsis* suggest that they may have differential enzymatic efficiencies. Several previous studies have also reported differential efficiencies of higher plant desaturases. For example, FAD2-1A and FAD2-1B proteins of soybean share about 93% amino acids identity, and the latter has been shown to accumulate 2 to 4 fold more di-unsaturated FAs (18:2 & 16:2) in wild-type yeast at higher or lower temperature [34].

For the soybean studies disclosed herein, FAD2-1B was used which shares 66% identity with *Arabidopsis* FAD2 protein sequence (data not shown). Such divergence may explain the significantly higher levels of both 18:1 and 16:1 desaturation by soybean FAD2 (FAD2-1B). In another study, the expression of soybean's two different FADS genes viz. FAD3-1A and FAD3-1B in wild type yeast was shown to accumulate 10.7 and 3.7% 18:3 respectively [39], although their predicted protein sequences were more than 93% identical. The soybean FAD3 (FAD3-1A) used in the present disclosure shares 66.6% identity with *Arabidopsis* FAD3 protein (data not shown). The Observed 30 to 40 fold higher 18:3 accumulation in mutant cb5 and wild-type yeast respectively by soybean FADS (FIG. 5) as compared to *Arabidopsis* FAD3 (FIG. 6), may be due to inherent variation in these proteins which originate from two diverged species. The same reason may also explain the lack of delta-12 desaturation activity in *Arabidopsis* FAD3 as compared to soybean FAD3.

It is interesting to note that among ER-localized proteins, fatty acid desaturases (FADs) have much shorter half-life as compared to other ER resident proteins. For example, mammalian ER-resident stearoyl-CoA desaturase, which is structurally related to plant FAD2/FAD3 enzyme families, has half-life of 4 hour compared to 2-6 days of ER-resident Cb5 proteins [42 and references therein]. It has been well documented that the half-life of ER resident FADs proteins can be modulated by environmental factors. For example, enhancement in unsaturation at cold temperature by higher plant FAD2 [34] and FAD3 [26] in heterologous yeast system were not correlated to any increase in their transcripts but to increase in the steady state level of respective desaturases. By analogy with above examples, it seems probable that an increase in abundance of soybean FAD3 protein together with its greater interaction efficiency with yeast Cb5 could have resulted in non-discrimination in 18:3 levels among soybean Cb5 isoforms observed specifically at lower temperature condition (FIG. 5B). Moreover, the attainment of relatively similar 18:3 level in *Arabidopsis* Cb5-A to that of both Cb5-E & Cb5-B when co-expressed with their native FADS, particularly at lower temperature condition (FIG. 6B) also suggests that probable increase in abundance in FAD3 might have contributed to less discrimination in their 18:3 levels. The lesser ω-3 desaturation efficiency of 'C' class of Cb5 proteins, whether from soybean (GmCb5-C2 & GmCb5-C3) or *Arabidopsis* (AtCb5-C), was observed with *Arabidopsis* FADS (AtFAD3) but not with soybean FAD3 (GmFAD3). These differences may explain why no substantial increase in 18:3 level with *Arabidopsis* Cb5-C with native FADS was observed at lower temperature conditions (FIG. 6B) and may also explain the display of relatively similar 18:3 level in

*Arabidopsis* Cb5-C (AtCb5-C) to that of AtCb5-B under condition with non-native soybean FADS (GmFAD3) at lower temperature (FIG. 7B).

The methods and materials described herein relate to genes and proteins which are implicated in controlling seed oil content in plants. According to this disclosure, plants may be genetically modified to have their seed oil content altered. The teem "genetically modify" is used to referred to an act of changing the trait of a plant, either by traditional breeding or by transgenic or targeted disruption of certain gene(s). These genes and proteins may be introduced into host plants to obtain plants that produce and store more or less oil in the seeds.

As used herein, "gene" refers to a nucleic acid sequence encoding a protein or a polypeptide. The broad definition of a gene may encompass the promoter region the intron and exon regions and untranslated regions located 3' or 5' to the coding sequence which are relevant to the expression of the gene product.

As used herein, "genotype" refers to the genetic constitution of a cell or organism.

As used herein, "phenotype" refers to the detectable characteristics of a cell or organism, which characteristics are the manifestation of gene expressions in said cell or organism.

For purpose of this disclosure, non-genetically modified (non-GMO) means reasonably capable of occurring in nature. An organism is considered non-GMO if it has not been genetically engineered to alter the genetic constitution of the organism. Genetic engineering may be through the addition of a gene or a fragment thereof in the form of recombinant nucleic acid, such as a transgene, by deletion of certain polynucleic acid from the organism, or by altering the sequence or the expression levels of a gene endogenous to the organism.

As used herein, "crossing", as used herein, refers to the mating of two parental strains.

A "fatty acid" (or "FA") is a carboxylic acid that generally has a long unbranched aliphatic hydrocarbon chain. The designations (18:2), (18:1), (18:3), etc., refer to the number of carbon atoms in the fatty acid chain and the number of double bonds therein, respectively. For example, oleic acid (18:1) contains 18 carbon atoms and 1 double bond. Exemplary fatty acids include:
  omega-3 fatty acids such as:
    alpha-linolenic acid $(CH_3(CH_2CH=CH)_3(CH_2)_7COOH)$
  omega-6 fatty acids such as:
    linoleic acid $(CH_3(CH_2)_4CH=CHCH_2CH=CH(CH_2)_7COOH)$
  omega-9 fatty acids such as:
    oleic acid $(CH_3(CH_2)_7CH=CH(CH_2)_7COOH)$
  and saturated fatty acids such as:
    palmitic acid $(CH_3(CH_2)_{14}COOH)$
    stearic acid $(CH_3(CH_2)_8COOH)$.

An isolated nucleic acid, as used herein, means a nucleic acid that is free of at least some of the contaminants associated with the nucleic acid occurring in a natural environment. An isolated nucleic acid may include DNA from which the introns are removed.

For a polynucleotide, the terms "mutation" or "mutated" refer to deletion or insertion of one or more nucleotide, substitutions of one or more nucleotide by different nucleotides. For a coding sequence, a mutation may or may not cause any change in the encoded polypeptide. Similarly, for a polypeptide, a mutation may be deletion or insertion of one or more amino acids, substitutions of one or more amino acid by different amino acids.

Mutations in isolated polynucleic acids may be made by techniques known in the art such as, but not limited to, site directed mutagenesis. Mutations may also be induced by X-ray, gamma ray or fast neutron irradiation, and treatment with chemical mutagens such as the alkylating agents ethylmethanesulfonate (EMS) or N-nitroso-N-methylurea in addition, natural genetic variation can result from mutations that arise from random DNA polymerase errors that occur during DNA replication of a plant genome. Natural genetic variation in plants may also result from activation of DNA repair mechanisms after exposure to natural sources of ionizing or nonionizing radiation.

A plant may be used in whole or in part. Preferred plant parts include reproductive or storage parts. The term "plant parts" as used herein includes, without limitation, seed, endosperm, ovule, pollen, roots, tubers, stems, leaves, stalks, fruit, berries, nuts, bark, pods, seeds and flowers. In an embodiment of the present disclosure, the plant part is the seeds.

The expression of a protein is generally regulated by a non-coding region of a gene termed a promoter. When a promoter controls the transcription of a gene, it can also be said that the expression of the gene (or the encoded protein) is driven by the promoter. When a promoter is placed in proximity of a coding sequence, such that transcription of the coding sequence is under control of the promoter, it can be said that the coding sequence is operably linked to the promoter. A promoter that is not normally associated with a gene is called a heterologous promoter. When a promoter only turns on the expression of certain genes in a specific tissue, such a promoter is called a tissue specific promoter.

The terms "protein," "polypeptide," and "peptide" may be used interchangeably in this disclosure, all of which refer to polymers of amino acids. In addition to the peptides explicitly disclosed herein, certain "conservative" mutations may be made on these peptides without significantly altering the functionality of the peptides.

As generally understood in the art, conserved amino acid residues among orthololgous proteins are the result of evolutionary pressure to maintain biological function and/or folding the protein. An amino acid position conserved among orthologous sets of genes can be involved in many aspects of structure and function. Invariant positions, or those showing conservation of certain residue properties (e.g. charge, hydrophobicity, etc.) are less likely to tolerate mutations than those where the protein family permits mutations to a great variety of amino acids. Positional amino acid sequence conservation based on database sequence deposits, for example, is useful in the determination of amino acid substitutions that may have a deleterious effect on protein folding and/or biological function.

Computer algorithmic sequence alignment programs may be used to predict whether an amino acid substitution affects protein function based on sequence homology and the physical properties of amino acids. Amino acid substitution prediction methods such as, but not limited to, SIFT, PolyPhen, SNPs3D, PANTHER PSEC, PMUT and TopoSNP may be used to predict the effect of an amino acid substitution on protein function.

Conservative amino acid substitutions are generally defined as the replacement of one or more amino acids for a different amino acid or amino acids, that preserve the structural and functional properties of proteins.

"Non-conservative" substitutions of one amino acid for another are substitutions of amino acids having dissimilar structural and/or chemical properties, and are generally based on differences in polarity, charge, hydrophobicity, hydrophilicity and/or the amphipathic nature of the residues involved. The substituting amino acids may include naturally occurring amino acids as well as those amino acids that are not normally present in proteins that exist in nature.

EXAMPLES

The following nonlimiting examples report general procedures, reagents and characterization methods that teach by way of example, and should not be construed in a narrowing manner that limits the disclosure to what is specifically disclosed. Those skilled in the art will understand that numerous modifications may be made and still the result will fall within the spirit and scope of the present invention.

Example 1

Identification, Cloning and Expression Pattern of Soybean Cb5 Genes

The public release of nearly complete genome sequence of soybean (*Glycine max* var. Williams; also available at www-.phytozome.org) enabled us to explore Cb5 genes on genome-wide scale. When deduced protein of *Arabidopsis* Cb5 (At5g53560) was used as query to TBLASTN whole soybean genome, eleven promising Cb5 candidates were identified (Table 2).

TABLE 2

Cytochrome b5 (Cb5) genes of soybean
(*Glycine max* var Williams)

| Name | SEQ ID. No. | Sequence Accession Number |
|---|---|---|
| GmCb5-A1 | 1 | Gm0096x00349.2 |
| GmCb5-A2 | 11 | Gm0065x00536.3 |
| GmCb5-B1 | 12 | Gm0119x00133 |
| GmCb5-B2 | 13 | Gm0151x00024 |
| GmCb5-E1 | 4 | Gm0024x00061 |
| GmCb5-E2 | 14 | Gm0037x00062 |
| GmCb5-C1 | 15 | Gm0149x00147.2 |
| GmCb5-C2 | 2 | Gm0161x00053.2 |
| GmCb5-C3 | 3 | Gm0041x00751 |
| GmCb5-C4 | 16 | Gm0076x00051.1 |
| GmCb5-D | 17 | Gm0096x00363 |

The predicted protein sequence of soybean Cb5 ORFs (Glyma0 model) shared diagnostic heme-binding motif (-HPGGD-), essential for Cb5 function (data not shown). FIG. 1 shows the phylogenetic relationship of soybean (*Glycine max*) Cb5 proteins. All the soybean Cb5 proteins clustered with known ER targeted Cb5 proteins of Tung [19] and *Arabidopsis* [31], except GmCb5-D (FIG. 1). The GmCb5-D clustered with the known outer mitochondrial membrane targeted Cb5 protein of Ding [19] and *Arabidopsis* [19, 31] respectively. The Cb5 protein sequences were aligned using clustalX version 2.0 [45] with the default parameters (gap open penalty=10, gap extension penalty=0.2). The phylogenetic tree, rooted with yeast Cb5 (ScCb5) was constructed by the neighbour-joining method using MEGA4 software [46]. The percentage of bootstrap values (1000 replicates) is shown at the branch nodes. Accession numbers of soybean Cb5s are provided in Table 1. Accession number of *Arabidopsis* Cb5: AtCb5-A (At5g53560) (SEQ ID No. 5), AtCb5-B (At5g48810) (SEQ ID No. 6), AtCb5-C (At2g46650) (SEQ ID No. 7) and AtCb5-E (At2g32720) (SEQ ID No. 8). Accession number of Tung Cb5: Tung Cb5-A (AY578727) (SEQ ID No. 18), TungCb5-B (AY578728) (SEQ ID No. 19) and TungCb5-C (AY578729) (SEQ ID No. 20). Cb5=Cytochrome b5; At=*Arabidopsis thaliana*; Gm=*Glycine max*; Sc=*Saccharomyces cerevisiae*). The soybean GmCb5-B1 and GmCb5-B2 were removed from the phylogram. The sequences of four of the soybean Cb5 genes are shown in FIG. 10.

DNA cloning were conducted according to commonly used methods in the art. Briefly, total RNA from leaf and seed tissues of soybean (*Glycine max* var. Williams) were isolated using TRIZOL reagent (Invitrogen, USA). From *Arabidopsis* leaf tissue, total RNA was isolated by RNAqueous kit (Ambion, cat #1912). The RNA was treated with DNaseI (Turbo DNA-free DNaseI, Ambion) according to the manufacturer's instructions to remove genomic DNA contamination. The concentration of DNaseI treated RNA was determined with the NanoDrop ND-1000 UV-V is spectrophotometer (NanoDrop Technologies, Wilmington, Del., USA) and known amount of RNA was used to generate cDNA pool using oligo (dt)$_{12-18}$ and Superscript III reverse transcriptase (Invitrogen. USA) by following manufacturer's protocol. To simplify subsequent directional cloning, the primers of soybean Cb5 genes included restriction site BamH1/Sal1 at 5'- and HindIII at 3'-end respectively and for FAD2 & FAD3 ClaI & SacI at 5' & 3' end respectively. Similarly primers for *Arabidopsis* Cb5 included 5' BamH1 and 3' HindIII and for FAD2 & FAD3 Not1 & Pad1 at 5' & 3' end respectively. The primers for amplification of soybean and *Arabipdosis* Cb5 genes are included in Table 3 and Table 4, respectively. The cDNAs of respective genes were amplified by KOD hot start DNA polymerase (Novagen, USA) as per manufacturer's protocol by using gene-specific primers. The cDNAs were initially cloned in pKS(−) at EcoRV site and their sequences were verified by bidirectional sequencing. From sequence verified clones, the cDNA inserts were subsequently excised and cloned directionally in yeast expression vector pESc-URA (Stratagene, USA). Plasmids were constructed by standard molecular biology techniques [43]. The Cb5 genes of both soybean and *Arabidopsis* were cloned behind galactose-inducible GAL1 promoter whereas their FAD2/FAD3 were placed behind galactose-inducible GAL10 promoter,

TABLE 3

Primers used for clonining of
Cb5, FAD2 and FAD3 of soybean

| Genes | Forward* | Reverse* |
|---|---|---|
| Cb5-A1 | AATT<u>GGATCC</u>ATGGCTTC AGATCGG (SEQ ID 21) | AATT<u>AAGCTT</u>CTACTCTTTC TTGGTGTAGTG (SEQ ID 22) |
| Cb5-C2 | AATT<u>GGATCC</u>ATGGGTTC AAAAACCAAGAC (SEQ ID 23) | AATT<u>AAGCTT</u>TCAATTTTC TGACTCAGTG (SEQ ID 24) |
| Cb5-C3 | AATT<u>GGATCC</u>ATGGCCTC AAATCCCAAAAC (SEQ ID 25) | AATT<u>AAGCTT</u>TCATGAGGT GCTAGCATG (SEQ ID 26) |
| Cb5-E1 | AATT<u>GTCGAC</u>ATGGGTGG GGAGCGGAAC (SEQ ID 27) | AATT<u>AAGCTT</u>TTATGTTGA TTTGGTGTAGAAAC (SEQ ID 28) |
| FAD2-1B | AATT<u>ATCGAT</u>ATGGGTCT AGCAAAGGAAAC (SEQ ID 29) | AATT<u>GAGCTC</u>TCAATACT TGTTCCTGTAC (SEQ ID 30) |
| FAD3-1A | AATT<u>ATCGAT</u>ATGGTTAA AGACACAAAGC (SEQ ID 31) | AATT<u>GAGCTC</u>TCAGTCTC GGTGCGAGTG (SEQ ID 32) |

*The underlined sequences indicate restriction sites to facilitate cloning into yeast expression vector pESC (Stratagene).

TABLE 4

Primers used for clonining of Cb5, FAD2 and FAD3 of Arabipdosis

| Gene | Forward* | Reverse* |
|---|---|---|
| Cb5-A | AATTGGATCCATGTCTT CAGATCGGAAG (SEQ ID 33) | AATTAAGCTTCTAGTCT TTCTTGGTATAGTG (SEQ ID 34) |
| Cb5-B | AATTGGATCCATGGGCG GAGACGGA (SEQ ID 35) | AATTAAGCTTTCAAGAA GAAGGAGCCTTG (SEQ ID 36) |
| Cb5-C | AATTGGATCCATGGCGA ATCTAATTTCG (SEQ ID 37) | AATTAAGCTTGTTATTA CCAACAAACG( SEQ ID 38) |
| Cb5-E | AATTGGATCCACAAGAA TCAAACAAACA (SEQ ID 39) | AATTAAGCTTACTTGAA TCTTTCTCTC (SEQ ID 40) |
| FAD2 | AATTGCGGCCGCATGGG TGCAGGTGGAAGAATG (SEQ ID 41) | AACCTTAATTAATCATAA CTTATTGTTGTACCAG (SEQ ID 42) |
| FAD3 | AATTGCGGCCGCATGGT TGTTGCTATGGACCAAC (SEQ ID 43) | AACCTTAATTAATTAAT TGATTTTAGATTTGTC (SEQ ID 44) |

*The underlined sequences indicate restriction sites to facilitate cloning into yeast expression vector pESC (Strategene).

TABLE 5

Primers of soybean Cb5 (GmCb5) genes used for RT-PCR analysis

| Genes | Forward | Reverse |
|---|---|---|
| GmCb5-A1 | TCGGAAACTTCACACTTTT (SEQ ID 45) | TCACAAATTCTGGAGTCTTA (SEQ ID 46) |
| GmCb5-A2 | TCGGAAACTTCACACTTTC (SEQ ID 47) | TCACAAATTCTGGAGTCTTG (SEQ ID 48) |
| GmCb5-C1 | ATGGGTTCAAAAACCAAGAC (SEQ ID 49) | TCAATTTTCTGACTTGC (SEQ ID 50) |
| GmCb5-C2 | ATGGGTTCAAAAACCAAGAC (SEQ ID 49) | TCAATTTTCTGACTCAGTG (SEQ ID 51) |
| GmCb5-C3 | CTTTGAGGAGGTAGCTAAG (SEQ ID 52) | TGCGAGGCCCAGTATCAAC (SEQ ID 53) |
| GmCb5-C4 | TTTTGAGGAGGTGGCTAAT (SEQ ID 54) | GGCAAGGCCCAATATCAAG (SEQ ID 55) |
| GmCb5-E1 | ATGGGTGGGGAGCGGAAC (SEQ ID 56) | TTATGTTGATTTGGTGTAG AAAC (SEQ ID 57) |
| GmCb5-E2 | ATGGGTGGGGAGCGC (SEQ ID 58) | TCATGTTGATTTGGTGTAG AAACGAATG (SEQ ID 59) |
| Ef-1α | CAGACTCGTGAACATGCTC TGC (SEQ ID 60) | TACCTGGCCTTGGAATACTTGG (SEQ ID 61) |

Semi-quantitative RT-PCR was performed by following the procedures below: Organ specific expression patterns for each Cb5 gene of soybean were analyzed by semi-quantitative RT-PCR (30, Shockey et al). The DNaseI digested RNA of seeds (early R5), roots, young leaves and flowers were quantified by Nano-drop and equal quantities of RNA were used as template for RT-PCR reaction essentially as described above. The product of RT was diluted with equal volume of water and 4 μL of each di kited reaction was used as template in a 20 μL PCR reaction containing gene-specific primers (Table 5). The amplification conditions were as follows: 94° C. 3 min, and 2.9 cycles of 94° C. for 30s, 55° C. for 30s, and 72° C. for 1 min. Following PCR, the products were diluted further with 10 μL of water & loading dye and one third volume of each diluted reaction was analyzed by agarose gel electrophoresis. The degree of gene expression correlated to the relative intensity of each band as determined by visual comparison of the ethidium bromide staining intensity. The elongation factor Ef-1α gene [44] was used as positive control.

All GmCb5 genes except GmCb5-B1& GmCb5-B2 were amplified. Expression profiling utilizing semi-quantitative RT-PCR was then performed using the gene-specific primers sets (Table 5) to determine the transcript abundance of eight GmCb5 genes in different organs of soybean, namely roots, leaves, flowers and immature seeds (R5 stage). Notably, despite constitutive pattern of expression displayed by all GmCb5 genes, the expression of GmCb5-A1 and GmCb5-E7 were higher than others in all the organs including seed, the site of storage TAG synthesis (FIG. 2). Equal quantities of total RNA from each organ or tissue were analyzed for expression of each Cb5 gene by semi-quantitative RT-PCR using gene-specific primer pairs. The Ef-1α gene was used as a positive control. Publicly available soybean ESTs databases were searched for ESTs of GmCb5-B1 & GmCb5-B2 genes [32]. The ESTs of all GmCb5 genes were identified, including GmCb5-T) except GmCb5-B1 & GmCb5-B2 (data not shown).

The nucleotide sequence of cDNAs of cloned Cb5 genes viz. GmCb5-A1, GmCb5-E1, GmCb5-C1, GmCb5-C2 and GmCb5-C3 were identical to the published sequences (Glyma0 model). In GmCb52-E2, six sequence discrepancies were identified in its nucleotide sequence as compared to those published sequences. Due to the degeneracy of the genetic codes, the deduced protein sequences of these genes remained identical to published amino acids sequence. The members of each gene pair viz. GmCb5-E1& GmCb52-E2 and GmCb5-C1 & GmCb5-C2 are more than 94% identical to each other at their nucleotide level. Based on these results and the sequence information of Cb5 ORFs (Glyma0 model, www.phytozome.org), the members of each gene pair viz. GmCb5-A1 & GmCb5-A2 and GmCb5-C3& GmCb5-C4 are more than ~94% identical to each other at their nucleotide level. However, the overall nucleotide identity between the two gene pair viz. GmCb5-C1 & GmCb5-C2 and GmCb5-C3 & GmCb5-C4 are approximately 63%.

The demonstration of differential pattern of expression by members of the each of the four GmCb5 gene pairs viz. GmCb5-A1 & GmCb5-A2, GmCb5-C1 & GmCb5-C2, GmCb5-C3& GmCb5-C4 and GmCb5-E1 & GmCb52-E2 (FIG. 2) together with greater identity in nucleotide sequences between members of each gene pair not only suggested their differential upstream regulation but also indicated that every other likely paralog of each gene pair might have evolved by gene duplication event. Moreover, soybean is predicted to have eight ER Cb5 proteins (FIG. 1) as compared to three in *Tung* [19] and four in *Arabidopsis* [31].

Example 2

Functional Characterization of Soybean Cb5 Genes in Yeast

Yeast is an excellent experimental system to study FA desaturation as it provides a eukaryotic ER, Cb5, and NADH: cytochrome b5 reductase [25]. Moreover, FA profile of yeast cells are simple, lacks PUFAs typically found in plant oils [28] and can easily take up exogenously supplied FA.

Yeast Strains, transformation and culture conditions are as described below. The yeast strains used in this study included *Saccharomyces cerevisiae* Hansen (matα his3 leu2 lys2 ura3; cat #95400.13Y4742, Invitrogen) and the mutant strain that carried disruption in microsomal Cb5 gene (cat #95400.17382) in same above genetic background. Yeasts were transformed by Fast-Yeast Transformation kit (G-Bioscience, MO, USA) according to manufacturer's protocol. Transformants were selected from minimal SD agar (Clontech, cat #630412) plate supplemented with appropriate auxotrophic supplements (-URA DO mixture, Clontech, cat #630416) maintained at 30° C. The identities of different yeast transformants were verified once again using gene-specific primers. Individual colonies of transformed cells were then grown for 2 days at 30° C. in minimal SD media (Clontech, cat #630411) lacking uracil to generate preculture ($OD_{600}$~1.4-1.5). The amount of preculture necessary to obtain an $OD_{600}$ of 0.2 in 6 mL of induction media (SD Gal/Raf, Clontech, cat #630420) was pelleted at 1800×g for 5 minutes at +4° C. The pellets were washed once with 3 mL of induction media. The washed pellets were finally resuspended in 6 mL of induction media and incubated either at 28° C. for 48 h or 15° C. for 96 h with shaking at 250 rpm. The 18:2 (Nu-Chek Prep, Elysian, M N) when included, were added to the induction medium at a final concentration of 0.05% (v/v) along with 0.2% tergitol type NP-40 (Sigma) in order to solubilise fatty acids.

Fatty acid analysis was performed according to commonly used methodology. Briefly, to analyze fatty acids, 5 mL of induced yeast cultures ($OD_{600}$~1.4-1.5) were harvested by centrifugation. The pellets were subsequently washed once with 3 ml, of water and dried under vacuum. Cultures supplemented with exogenous FAs were washed first with 3 mL of 0.2% (v/v) tergitol type NP-40 (Sigma) and then twice with water. FAs analyses were performed as described [15]. Briefly, to the washed pellets 1 mL of 2.5% sulfuric acid (v/v) in methanol and a known amount of 17:0 as internal standard were added and incubated at 80° C. for an hour. After cooling, FAMES were recovered in 200 µl, of hexane and 1 µL was injected (split ratio 10:1) on GC (Trace GC ultra, Thermo Electron Corporation) fitted with a 30-m×0.25-mm (i.d.) TR-FAME column (Thermo Electron Corporation) and quantified using a flame ionization detector. The GC oven temperature was programmed to hold at 150° C. for 1 min, increase to 180° C. at 10° C. per min, and then hold for an additional 6 min, Identification of peaks were confirmed with commercially available methyl esters of standards (Nu-Chek Prep, Elysian, Minn.). All analyses were performed on triplicate samples and replicated three times.

Figure 3:
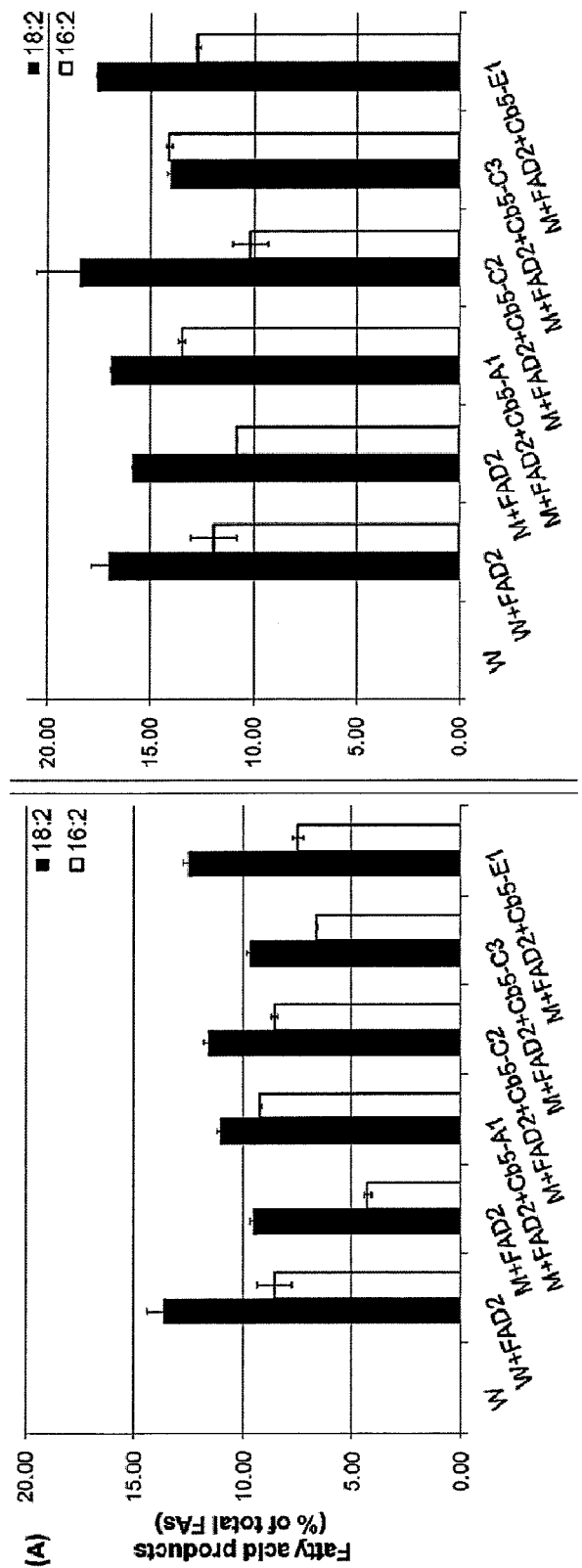
FIG. 3 shows the 16:2 and 18:2 content of yeast co-expressing Cb5 and FAD2 of soybean.

In order to determine whether cDNA encoded proteins of soybean Cb5 ORFs were capable of FA desaturation; soybean Cb5 ORFs were co-expressed individually with native FAD2-1B [34] in mutant cb5 yeast lacking endogenous Cb5 gene. FIG. 3 shows the 16:2 and 18:2 content of yeast co-expressing Cb5 and FAD2 of soybean. Yeast cultures were induced with galactose and allowed to grow at 28° C. for 48 h (A) and at 15° C. for 96 h (B). FAMES were analyzed by GC-FID. Values are expressed as molar percentage of total FAs and represent average and SD of three independent cultures. W=wild type yeast (empty vector pESC control); M=mutant cb5 yeast.

The production of total di-unsaturated FAs (18:2 and 16:2) in mutant cb5 yeast was less than the wild type (FIG. 3A) but even their considerable production could possibly be due to interaction of FAD2 (FAD2-1B) with the functional Cb5 domain of stearoyl CoA desaturase [35]. In mutant cb5 yeast co-expressing Cb5 genes and FAD2, moderate increase in their total di-unsaturated FAs levels was observed compared to those expressing FAD2 only. The above result unequivocally demonstrated functionality of Cb5 proteins in complementing the defects of mutant cb5 yeast; however, the insignificant difference in total di-unsaturated FAs levels among four different Cb5 isoforms suggested that these proteins have relatively similar ω-6 desaturation efficiencies. Similar result was obtained in a previous study where no major difference in ω-6 desaturation product was observed with four Cb5 isoforms of *Tung* [19].

Under heterologous yeast expression system the improvement in desaturation efficiency at lower temperature leading to enhanced production of unsaturated fatty acids has been demonstrated by many higher plant desaturases such as FAD2 of *Arabidopsis* [24] or soybean [34], FAD3 of *Brassica napus* [26]. Consistent with the above results, ~1.5 fold increase in total di-unsaturated FAs levels was also observed at reduced temperature (FIG. 3B). Here again, the levels of total di-unsaturated FAs among Cb5 isoforms were relatively similar. It is interesting to note that at reduced temperature the total di-unsaturated FA levels in mutant cb5 yeast expressing FAD2 gene alone became relatively similar to those co-expressing Cb5 & FAD2 and also to the wild type strain expressing FAD2. Moreover, the demonstration of relatively similar level of di-unsaturated FAs accumulation by isoforms of each pair viz. Cb5-C1 & Cb5-C2 and Cb5-E1 & Cb5-E2 (data not shown) was not unexpected with the given higher level of amino acid identity between members of each pair.

The higher plant FAD2 was capable of desaturating both 16:1 as well as 18:1 [24, 36] and in wild type yeast with the availability of nearly similar levels of mono-unsaturates *Arabidopsis* FAD2 produces roughly 7.5 times as much 18:2 as 16:2 [3]. However, with soybean FAD2, about 1.5 times as much 18:2 as 16:2 in wild type yeast was observed (FIG. 3). Such a higher level of 16:1 desaturation by soybean FAD2 and not with *Arabidopsis* FAD2 (see below) indicated the broader substrate preference of soybean FAD2.

Example 3

*Arabidopsis* Cb5 Isoforms Exhibits Differential ω-6 Desaturation

*Arabidopsis* has six annotated Cb5 genes at TAM database (www.tair.org) and based on direct and indirect evidence regarding their FR localization [18, 22, 31, 37], four genes viz. Cb5-A (At5g53560), Cb5-B (At5g48810), Cb5-C (At2g46650) & Cb5-E (At2g32720) were selected for this study. Whose sequences are shown in FIG. 11. Among the other two Cb5 genes i.e. Cb5-D (At1g26340) and Cb5-F (At1g60660), the former is targeted to outer mitochondrial membrane [31] and the later is quite distinct in having a predicted transmembrane domain at its N-termini as opposed to C-termini typically found with Cb5 proteins [9]. The *Arabidopsis* Cb5 genes have been implicated in ER based FA desaturation [14] but prior to this study direct evidence regarding their individual contribution in FAs desaturation was lacking. The significant production of di-unsaturated FAs (18:2 & 16:2) in mutant cb5 yeast co-expressing Cb5 genes and native FAD2 (At3g12120) as compared to those expressing FAD2 only was not an unexpected outcome. However, significant variation among four Cb5 isoforms in their di-unsaturated FAs levels was observed.

Figure 4:
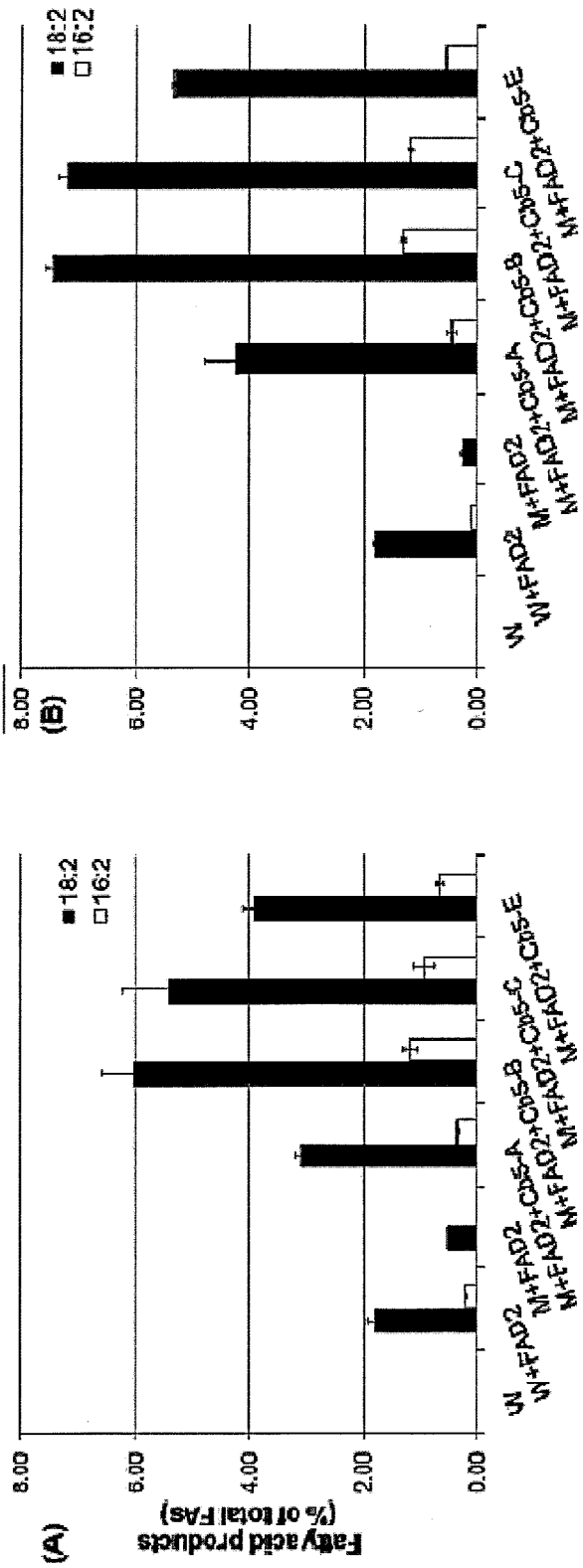
FIG. 4 shows the 16:2 and 18:2 content of yeast co-expressing Cb5 and FAD2 of *Arabidopsis*.

FIG. 4 shows the 16:2 and 18:2 content of yeast co-expressing Cb5 and FAD2 of *Arabidopsis*. The experimental conditions were the same as those described in FIG. 3. W=wild type yeast (empty vector pESC control); M=mutant cb5 yeast. Both Cb5-B & Cb5-C were able to accumulate ~1.5 to 2 fold more di-unsaturated FAs than Cb5-E and Cb5-A, respectively (FIG. 4A). In spite of considerable enhancement in ω-6 desaturation products at lower temperature, both Cb5-B & Cb5-C were still able to accumulate ~1.5 fold more di-unsaturated FAs than Cb5-E and Cb5-A respectively, (FIG. 4B).

In heterologous expression system the products of desaturation depends on several factors such as growth conditions, temperature, substrate availability [24] yeast strain, concentration of galactose [38]. In our study, the expression of *Arabidopsis* FAD2 in wild type yeast consistently showed typical ~7 times as much 18:2 accumulation as 16:2, but the level of di-unsaturated FAs was 2% of total FAs as opposed to 20-40% reported in a previous study [38]. The above discrepancy could possibly be due to differences in yeast strain, growth conditions, expression vector or concentration of galactose in the media.

Example 4

Cb5 Isoforms of Soybean and *Arabidopsis* Modulate ω-3 Desaturation

In majority of angiosperms, FAD3 is mainly responsible for ω-3 FA production, and more particularly for 18:3 production. Accordingly, the contribution of various Cb5 isoforms in ω-3 desaturation were studied. Among four FAD3 genes of soybean, FAD3-1A [39] was used, which is similar to FAD3B [40]. FIG. 5 shows the 18:3 content of yeast co-expressing Cb5 and FAD3 of soybean. Known amount of 18:2 were added to cultures before induction with galactose and allowed to grow at 28° C. for 48 h (A) or at 15° C. for 96 h (4 FAMES were analyzed by GC-FID. Values are expressed as molar percentage of total FAs and represent average and SD of three independent cultures. W=wild type yeast (empty vector pESC control); M=mutant cb5 yeast. As expected, in FAD3 (FAD3-1a) transformed wild type or mutant cb5 yeast culture not supplemented with exogenous 18:2, we failed to detect 18:3 (Table 6), but under conditions of 18:2 feeding considerable production of 18:3 was observed in both wild type and mutant cb5 yeast (FIG. 5A).

TABLE 6

Fatty Acid composition of yeast co-expressing Cb5 and FAD2/FAD3 of Soybean

| | 16:0 | | 16:1 | | 16:2 | | 18:0 | |
|---|---|---|---|---|---|---|---|---|
| | 28° C. | 15° C. | 28° C. | 15° C. | 28° C. | 15° C. | 28° C. | 15° C. |
| W (empty pESC) | 23.9 ± 0.19 | 21.9 ± 0.09 | 38.2 ± 0.30 | 44.9 ± 0.05 | | | 9.6 ± 0.14 | 6.6 ± 0.11 |
| M (empty pESC) | 24.2 ± 0.27 | 21.1 ± 0.39 | 39.0 ± 0.40 | 45.2 ± 0.30 | | | 9.2 ± 0.10 | 6.6 ± 0.01 |
| W + FAD2 | 21.6 ± 0.07 | 19.0 ± 0.21 | 26.4 ± 1.02 | 27.6 ± 1.11 | 8.6 ± 0.80 | 11.9 ± 1.10 | 12.1 ± 0.10 | 8.6 ± 0.09 |
| M + FAD2 | 22.6 ± 0.12 | 18.7 ± 0.06 | 29.1 ± 0.21 | 30.1 ± 0.13 | 4.3 ± 0.15 | 10.8 ± 0.03 | 11.3 ± 0.03 | 8.1 ± 0.05 |
| M + FAD2 + Cb5-A1 | 20.4 ± 0.02 | 18.9 ± 0.05 | 29.7 ± 0.18 | 26.8 ± 0.05 | 9.2 ± 0.07 | 13.5 ± 0.16 | 8.9 ± 0.04 | 8.3 ± 0.04 |
| M + FAD2 + Cb5-C2 | 22.9 ± 0.05 | 14.9 ± 1.67 | 27.1 ± 0.34 | 25.2 ± 1.79 | 8.6 ± 0.18 | 10.2 ± 0.85 | 11.3 ± 0.07 | 10.7 ± 0.14 |
| M + FAD2 + Cb5-C3 | 20.6 ± 0.57 | 20.5 ± 0.07 | 26.6 ± 0.21 | 27.5 ± 0.12 | 6.6 ± 0.03 | 14.1 ± 0.13 | 13.6 ± 0.08 | 8.6 ± 0.11 |
| M + FAD2 + Cb5-E1 | 22.4 ± 0.12 | 18.8 ± 0.04 | 26.7 ± 0.41 | 26.2 ± 0.08 | 7.5 ± 0.23 | 12.7 ± 0.10 | 11.4 ± 0.11 | 8.6 ± 0.05 |
| W + FAD3* | 22.8 ± 0.12 | 20.5 ± 0.09 | 36.0 ± 0.02 | 42.7 ± 0.06 | 1.0 ± 0.05 | 1.6 ± 0.04 | 18.5 ± 0.08 | 6.9 ± 0.04 |
| M + FAD3* | 24.0 ± 0.04 | 17.0 ± 0.19 | 33.5 ± 0.08 | 41.4 ± 0.21 | 0.7 ± 0.01 | 1.6 ± 0.01 | 10.7 ± 0.04 | 7.4 ± 0.06 |
| W (empty pESC) | 23.9 ± 0.85 | 21.5 ± 0.45 | 4.2 ± 0.94 | 8.5 ± 0.45 | | | 8.7 ± 0.49 | 5.2 ± 0.07 |
| M (empty pESC) | 24.5 ± 0.59 | 20.9 ± 0.33 | 4.2 ± 0.95 | 8.5 ± 0.48 | | | 8.7 ± 0.32 | 4.8 ± 0.23 |
| W + FAD3 | 19.9 ± 1.02 | 19.1 ± 0.38 | 3.4 ± 0.37 | 7.4 ± 0.99 | 0.1 ± 0.01 | 0.1 ± 0.09 | 8.2 ± 0.56 | 5.1 ± 0.26 |
| M + FAD3 | 16.0 ± 4.63 | 13.5 ± 0.21 | 6.1 ± 3.25 | 12.0 ± 0.28 | 0.1 ± 0.04 | 0.3 ± 0.01 | 6.8 ± 2.09 | 4.8 ± 0.20 |
| M + FAD3 + Cb5-A1 | 15.6 ± 0.89 | 16.6 ± 0.24 | 2.6 ± 0.20 | 6.0 ± 0.13 | 0.2 ± 0.01 | 0.2 ± 0.01 | 6.7 ± 0.39 | 4.7 ± 0.11 |
| M + FAD3 + Cb5-C2 | 22.6 ± 0.48 | 17.8 ± 0.35 | 4.7 ± 0.57 | 5.8 ± 0.33 | 0.3 ± 0.07 | 0.2 ± 0.01 | 9.0 ± 0.19 | 4.7 ± 0.08 |
| M + FAD3 + Cb5-C3 | 20.5 ± 0.42 | 19.2 ± 0.19 | 4.3 ± 0.76 | 6.7 ± 0.15 | 0.2 ± 0.06 | 0.2 ± 0.01 | 10.8 ± 0.16 | 5.3 ± 0.11 |
| M + FAD3 + Cb5-E1 | 17.4 ± 1.73 | 16.3 ± 0.15 | 3.0 ± 0.69 | 6.1 ± 0.18 | 0.2 ± 0.05 | 0.2 ± 0.01 | 7.0 ± 0.84 | 4.5 ± 0.06 |

| | 18:1 | | 18:2 | | 18:3 | |
|---|---|---|---|---|---|---|
| | 28° C. | 15° C. | 28° C. | 15° C. | 28° C. | 15° C. |
| W (empty pESC) | 28.3 ± 0.44 | 26.5 ± 0.25 | | | | |
| M (empty pESC) | 27.6 ± 0.37 | 27.1 ± 0.11 | | | | |
| W + FAD2 | 17.7 ± 0.54 | 16.0 ± 0.66 | 13.7 ± 0.73 | 17.0 ± 0.85 | | |
| M + FAD2 | 23.2 ± 0.12 | 16.5 ± 0.02 | 9.5 ± 0.21 | 15.8 ± 0.05 | | |
| M + FAD2 + Cb5-A1 | 20.8 ± 0.09 | 15.7 ± 0.07 | 11.1 ± 0.17 | 16.9 ± 0.04 | | |
| M + FAD2 + Cb5-C2 | 18.6 ± 0.12 | 20.6 ± 0.83 | 11.6 ± 0.17 | 18.4 ± 2.12 | | |
| M + FAD2 + Cb5-C3 | 23.0 ± 0.06 | 15.3 ± 0.05 | 9.7 ± 0.12 | 14.0 ± 0.15 | | |
| M + FAD2 + Cb5-E1 | 19.5 ± 0.28 | 16.2 ± 0.03 | 12.5 ± 0.25 | 17.6 ± 0.06 | | |
| W + FAD3* | 29.1 ± 0.13 | 27.6 ± 0.24 | 0.5 ± 0.01 | 0.8 ± 0.02 | | |
| M + FAD3* | 30.8 ± 0.15 | 31.6 ± 0.04 | 0.4 ± 0.02 | 1.1 ± 0.01 | | |
| W (empty pESC) | 3.0 ± 0.72 | 4.7 ± 0.29 | 60.3 ± 3.00 | 60.2 ± 1.25 | | |
| M (empty pESC) | 2.8 ± 0.69 | 4.6 ± 0.30 | 59.8 ± 2.48 | 61.1 ± 1.18 | | |
| W + FAD3 | 2.7 ± 0.33 | 4.7 ± 0.72 | 57.4 ± 2.97 | 45.3 ± 2.89 | 8.3 ± 0.70 | 18.3 ± 1.17 |
| M + FAD3 | 5.7 ± 3.11 | 9.3 ± 0.27 | 59.5 ± 15.01 | 44.5 ± 1.08 | 5.9 ± 1.92 | 15.6 ± 0.37 |
| M + FAD3 + Cb5-A1 | 2.1 ± 0.17 | 3.9 ± 0.13 | 60.1 ± 2.36 | 49.8 ± 0.79 | 12.8 ± 0.75 | 18.7 ± 0.21 |
| M + FAD3 + Cb5-C2 | 3.6 ± 0.39 | 3.6 ± 0.20 | 43.5 ± 1.74 | 47.9 ± 1.29 | 16.2 ± 0.87 | 20.1 ± 0.33 |
| M + FAD3 + Cb5-C3 | 4.1 ± 0.70 | 4.2 ± 0.14 | 49.0 ± 2.35 | 43.7 ± 0.17 | 10.9 ± 0.24 | 20.7 ± 0.50 |
| M + FAD3 + Cb5-E1 | 2.4 ± 0.58 | 4.1 ± 0.10 | 54.6 ± 4.89 | 49.8 ± 1.03 | 15.4 ± 1.00 | 19.0 ± 0.56 |

For Cb5 and FAD3 co-expression study 18:2 were added to the culture before induction with galactose. FAMES were analyzed by GC-FID. Induction time for culture maintained at 28° C. and 15° C. were 48 and 96 hour respectively.
Values represents mol percentage of total fatty acids.
± represents SD of three independent cultures.
W = wild type yeast:
M = mutant yeast disrupted in endogenous Cb5 gene;
ND = Not detected.
*Clutures not fed with 18:2.

Notably, with co-expression of soybeans Cb5 genes and native FAD3, more than 2 fold increase in 18:3 production were observed in mutant cb5 yeast as compared to those expressing FAD3 alone (FIG. 5A). Along with the demonstration of nice complementation, we also observed interesting variation among Cb5 isoforms with respect to their 18:3 levels. Although 18:3 levels were relatively similar in Cb5-C2 and Cb5-E1, both showed ~1.5 fold more 18:3 accumulations than Cb5-C3. In Cb5-A1 the 18:3 levels was intermediate to that of Cb5-C2 & Cb5-E1 and Cb5-C respectively. At reduced temperature conditions the product of ω-3 desaturation improved significantly but on the contrary we failed to see distinct variation among Cb5 isoforms regarding their 18:3 levels (FIG. 5B).

On the other hand, as shown in FIG. 6, with co-expression of *Arabidopsis* Cb5 and native FAD3 (At2g29980) in mutant cb5 yeast, we similarly observed significant increase in 18:3 production compared to those expressing FAD3 alone (FIG. 6A). Experimental conditions were the same as those described in FIG. 5. W=wild type yeast (empty vector pESC control); M=mutant cb5 yeast. And similar to soybean, we also observed significant variation in 18:3 levels among Cb5 isoforms. Both Cb5-B & Cb5-E were able to accumulate 2 to 4 fold more 18:3 than Cb5-A and Cb5-C respectively. And even at reduced temperature conditions both Cb5-B & Cb5-E were still able to maintain ~2 fold higher 18:3 level than Cb5-C, but on the contrary, 18:3 level in Cb5-A became relatively similar to both Cb5-B & Cb5-E respectively (FIG. 6B).

TABLE 7

Fatty Acid composition of yeast co-expressing Cb5 and FAD2/FAD3 of *Arabidopsis*

| Constructs | 16:0 28° C. | 16:0 15° C. | 16:1 28° C. | 16:1 15° C. | 16:2 28° C. | 16:2 15° C. | 18:0 28° C. | 18:0 15° C. |
|---|---|---|---|---|---|---|---|---|
| W (empty pESC) | 23.9 ± 0.27 | 21.9 ± 0.09 | 39.0 ± 0.18 | 45.8 ± 0.09 | | | 9.3 ± 0.13 | 6.4 ± 0.04 |
| M (empty pESC) | 23.1 ± 0.08 | 21.5 ± 0.33 | 39.1 ± 0.69 | 46.0 ± 0.72 | | | 8.7 ± 0.11 | 6.1 ± 0.18 |
| W + FAD2 | 23.3 ± 0.22 | 21.9 ± 0.02 | 39.1 ± 0.34 | 45.1 ± 0.01 | 0.2 ± 0.03 | 0.1 ± 0.00 | 9.0 ± 0.14 | 6.3 ± 0.12 |
| M + FAD2 | 22.6 ± 0.10 | 22.0 ± 0.90 | 39.3 ± 0.28 | 46.0 ± 0.83 | ND | ND | 8.7 ± 0.07 | 6.1 ± 0.27 |
| M + FAD2 + Cb5-A | 22.4 ± 0.05 | 19.7 ± 0.25 | 39.5 ± 0.08 | 47.5 ± 0.23 | 0.4 ± 0.03 | 0.4 ± 0.07 | 8.8 ± 0.05 | 5.9 ± 0.19 |
| M + FAD2 + Cb5-B | 22.8 ± 0.12 | 22.5 ± 0.09 | 36.9 ± 0.17 | 43.1 ± 0.03 | 1.2 ± 0.13 | 1.3 ± 0.03 | 9.2 ± 0.22 | 6.7 ± 0.17 |
| M + FAD2 + Cb5-C | 22.9 ± 0.07 | 21.5 ± 0.03 | 38.1 ± 0.28 | 44.1 ± 0.17 | 0.9 ± 0.19 | 1.2 ± 0.04 | 9.0 ± 0.05 | 6.4 ± 0.07 |
| M + FAD2 + Cb5-E | 21.8 ± 0.05 | 18.2 ± 0.13 | 40.3 ± 0.14 | 47.7 ± 0.16 | 0.6 ± 0.06 | 0.5 ± 0.01 | 8.8 ± 0.13 | 6.6 ± 0.07 |
| W + FAD3* | 22.8 ± 0.28 | 21.4 ± 0.17 | 38.8 ± 0.52 | 45.7 ± 0.06 | | | 9.1 ± 0.30 | 6.0 ± 0.29 |
| M + FAD3* | 22.8 ± 0.29 | 21.2 ± 0.16 | 38.4 ± 0.21 | 46.0 ± 0.03 | | | 9.1 ± 0.15 | 6.1 ± 0.16 |
| W (empty pESC) | 21.9 ± 1.17 | 21.7 ± 0.13 | 2.6 ± 0.33 | 9.4 ± 0.17 | | | 7.6 ± 0.43 | 4.9 ± 0.08 |
| M (empty pESC) | 22.9 ± 0.29 | 21.5 ± 0.53 | 3.1 ± 0.26 | 8.7 ± 0.46 | | | 8.4 ± 0.14 | 4.7 ± 0.11 |
| W + FAD3 | 17.1 ± 2.18 | 20.7 ± 0.21 | 1.9 ± 0.41 | 7.7 ± 0.32 | | | 6.0 ± 0.80 | 4.5 ± 0.07 |
| M + FAD3 | 17.8 ± 0.76 | 21.2 ± 0.36 | 2.0 ± 0.20 | 8.3 ± 0.29 | | | 6.6 ± 0.04 | 4.6 ± 0.28 |
| M + FAD3 + Cb5-A | 15.5 ± 0.30 | 17.6 ± 0.90 | 2.7 ± 0.10 | 7.6 ± 0.36 | | | 5.9 ± 0.03 | 4.4 ± 0.48 |
| M + FAD3 + Cb5-B | 16.9 ± 0.59 | 19.0 ± 0.37 | 2.2 ± 0.02 | 6.1 ± 0.47 | | | 6.2 ± 0.26 | 4.6 ± 0.06 |
| M + FAD3 + Cb5-C | 19.4 ± 0.88 | 19.2 ± 0.82 | 2.6 ± 0.19 | 6.2 ± 0.57 | | | 7.3 ± 0.10 | 4.7 ± 0.41 |
| M + FAD3 + Cb5-E | 17.8 ± 0.65 | 18.7 ± 0.30 | 2.8 ± 0.11 | 9.0 ± 0.45 | | | 6.9 ± 0.14 | 5.3 ± 0.21 |

| Constructs | 18:1 28° C. | 18:1 15° C. | 18:2 28° C. | 18:2 15° C. | 18:3 28° C. | 18:3 15° C. |
|---|---|---|---|---|---|---|
| W (empty pESC) | 27.8 ± 0.33 | 25.9 ± 0.16 | | | | |
| M (empty pESC) | 29.1 ± 0.65 | 26.3 ± 0.27 | | | | |
| W + FAD2 | 26.6 ± 0.01 | 24.8 ± 0.15 | 1.6 ± 0.14 | 1.6 ± 0.03 | | |
| M + FAD2 | 28.8 ± 0.32 | 25.7 ± 0.31 | 0.5 ± 0.01 | 0.3 ± 0.03 | | |
| M + FAD2 + Cb5-A | 25.8 ± 0.20 | 22.2 ± 0.74 | 3.1 ± 0.16 | 4.3 ± 0.54 | | |
| M + FAD2 + Cb5-B | 23.9 ± 0.50 | 18.9 ± 0.04 | 6.0 ± 0.58 | 7.4 ± 0.16 | | |
| M + FAD2 + Cb5-C | 23.7 ± 0.86 | 19.6 ± 0.17 | 6.4 ± 0.84 | 7.2 ± 0.17 | | |
| M + FAD2 + Cb5-E | 24.5 ± 0.28 | 21.6 ± 0.12 | 3.9 ± 0.22 | 5.3 ± 0.04 | | |
| W + FAD3* | 29.3 ± 0.10 | 26.9 ± 0.40 | | | | |
| M + FAD3* | 29.7 ± 0.23 | 26.7 ± 0.34 | | | | |
| W (empty pESC) | 1.8 ± 0.20 | 4.4 ± 0.11 | 65.9 ± 2.11 | 60.6 ± 0.25 | | |
| M (empty pESC) | 2.1 ± 0.19 | 4.5 ± 0.27 | 63.3 ± 0.84 | 60.6 ± 1.32 | | |
| W + FAD3 | 1.3 ± 0.26 | 4.1 ± 0.15 | 73.4 ± 3.73 | 62.6 ± 0.63 | 0.3 ± 0.06 | 0.3 ± 0.01 |
| M + FAD3 | 1.2 ± 0.10 | 4.4 ± 0.19 | 72.1 ± 1.11 | 61.0 ± 1.09 | 0.3 ± 0.02 | 0.3 ± 0.01 |
| M + FAD3 + Cb5-A | 2.0 ± 0.05 | 4.6 ± 0.84 | 69.9 ± 0.46 | 54.5 ± 2.85 | 4.0 ± 0.05 | 11.4 ± 0.49 |
| M + FAD3 + Cb5-B | 1.4 ± 0.03 | 3.5 ± 0.22 | 65.2 ± 1.05 | 55.1 ± 1.43 | 8.2 ± 1.40 | 11.8 ± 0.42 |
| M + FAD3 + Cb5-C | 1.8 ± 0.15 | 3.4 ± 0.37 | 67.2 ± 1.16 | 61.3 ± 2.63 | 1.7 ± 0.15 | 5.2 ± 0.47 |
| M + FAD3 + Cb5-E | 2.0 ± 0.10 | 4.7 ± 0.20 | 62.3 ± 1.13 | 49.6 ± 2.82 | 8.2 ± 1.77 | 12.6 ± 1.66 |

For Cb5 and FAD3 co-expression study 18:2 were added to the culture before induction with galactose. FAMES were analyzed by GC-FID. Induction time for culture maintained at 28° C. and 15° C. were 48 and 96 hour respectively.
Values represents mol percentage of total fatty acids.
± represents SD of three independent cultures.
W = wild type yeast:
M = mutant yeast disrupted in endogenous Cb5 gene;
ND = Not detected.
*Clutures not fed with 18:2.

Higher plants FAD3 possess a minor activity to desaturate mono-unsaturated FAs (16:1 and 18:1). In a previous study the expression of *Brassica napus* FAD3 in wild type yeast was shown to accumulate minor but distinct 16:2 (Δ9, 13) and 18:2 (Δ9,15) FAs [25]. In our study, with soybean FAD3 expression in both wild type and mutant cb5 yeast we similarly observed minor 16:2 and 18:2 FAs (Table 6) but their retention time corresponded to 16:2 (Δ9, 12) and 18:2 (Δ9, 12) as obtained with soybean/*Arabidopsis* FAD2 expression, (Tables 6 & 7). These two FAs were completely absent in control samples of both wild type and mutant cb5 yeast transformed with empty vector. Under the condition of exogenous 18:2 feeding also, the 16:2 peak appeared consistently in both wild type or mutant cb5 yeast expressing soybean FAD3 alone or co-expressing with either native (Table 6) or non-native (Table 8) Cb5 respectively. The display of an inherent low level of delta-12 desaturase activity by soybean FAD3, as opposed to ω-3 desaturase activity reported for *Brassica napus* FAD3 could possibly be due to FAD3 originating from two diverged species.

TABLE 8

Fatty Acid composition of yeast co-expressing Cb5 of *Arabidopsis* (A) or soybean (B) with non-native FAD3 respectively

| Constructs | 16:0 28° C. | 16:0 15° C. | 16:1 28° C. | 16:1 15° C. | 16:2 28° C. | 16:2 15° C. | 18:0 28° C. | 18:0 15° C. |
|---|---|---|---|---|---|---|---|---|
| W (empty pESC) | 13.3 ± 0.43 | 16.7 ± 0.10 | 1.0 ± 0.05 | 4.7 ± 0.11 | | | 4.6 ± 0.11 | 3.9 ± 0.05 |
| A | | | | | | | | |
| W + GmFAD3 | 16.4 ± 1.83 | 15.2 ± 0.16 | 1.8 ± 0.36 | 5.6 ± 0.14 | ND | 0.2 ± 0.00 | 6.3 ± 0.63 | 4.2 ± 0.04 |
| M + GmFAD3 | 14.3 ± 0.58 | 17.3 ± 2.66 | 1.5 ± 0.08 | 5.8 ± 0.58 | ND | 0.2 ± 0.03 | 5.5 ± 0.30 | 4.7 ± 0.76 |
| M + GmFAD3 + AtCb5-A | 16.4 ± 1.27 | 17.2 ± 0.27 | 2.9 ± 0.34 | 7.4 ± 0.20 | 0.2 ± 0.02 | 0.3 ± 0.00 | 6.2 ± 0.55 | 4.7 ± 0.14 |
| M + GmFAD3 + AtCb5-B | 15.8 ± 0.11 | 17.6 ± 0.83 | 2.1 ± 0.07 | 7.9 ± 0.69 | 0.2 ± 0.03 | 0.3 ± 0.02 | 6.7 ± 0.11 | 4.7 ± 0.36 |
| M + GmFAD3 + AtCb5-C | 16.1 ± 2.44 | 17.6 ± 0.06 | 1.7 ± 0.42 | 5.3 ± 0.14 | 0.1 ± 0.02 | 0.3 ± 0.02 | 6.3 ± 0.99 | 4.9 ± 0.05 |
| M + GmFAD3 + AtCb5-E | 20.0 ± 0.20 | 19.2 ± 0.16 | 3.0 ± 0.12 | 8.9 ± 0.32 | 0.2 ± 0.01 | 0.5 ± 0.01 | 7.8 ± 0.06 | 5.8 ± 0.08 |
| B | | | | | | | | |
| W + AtFAD3 | 13.5 ± 0.68 | 17.6 ± 1.08 | 1.1 ± 0.05 | 5.4 ± 0.60 | | | 4.7 ± 0.33 | 4.3 ± 0.31 |
| M + AtFAD3 | 14.1 ± 0.93 | 17.9 ± 0.32 | 1.1 ± 0.07 | 5.2 ± 0.31 | | | 4.9 ± 0.33 | 4.5 ± 0.13 |
| M + AtFAD3 + GmCb5-A1 | 18.9 ± 1.05 | 21.5 ± 0.07 | 3.3 ± 0.33 | 9.8 ± 1.20 | | | 7.6 ± 0.66 | 6.0 ± 0.15 |
| M + AtFAD3 + GmCb5-C2 | 20.9 ± 0.39 | 21.7 ± 0.94 | 2.6 ± 0.06 | 10.1 ± 1.27 | | | 7.5 ± 0.17 | 6.1 ± 0.25 |
| M + AtFAD3 + GmCb5-C3 | 21.0 ± 0.21 | 23.2 ± 0.36 | 2.6 ± 0.07 | 12.8 ± 0.65 | | | 7.5 ± 0.14 | 5.5 ± 0.09 |
| M + AtFAD3 + GmCb5-E1 | 22.7 ± 0.78 | 23.2 ± 0.91 | 3.7 ± 0.49 | 11.6 ± 0.67 | | | 8.9 ± 0.32 | 5.8 ± 0.30 |

| Constructs | 18:1 28° C. | 18:1 15° C. | 18:2 28° C. | 18:2 15° C. | 18:3 28° C. | 18:3 15° C. |
|---|---|---|---|---|---|---|
| W (empty pESC) | 0.7 ± 0.04 | 2.6 ± 0.04 | 80.4 ± 0.62 | 72.0 ± 0.28 | | |
| A | | | | | | |
| W + GmFAD3 | 1.4 ± 0.27 | 3.7 ± 0.09 | 68.8 ± 3.13 | 54.8 ± 0.34 | 5.1 ± 0.95 | 16.3 ± 0.89 |
| M + GmFAD3 | 1.1 ± 0.07 | 3.9 ± 0.17 | 73.0 ± 1.15 | 52.4 ± 1.17 | 4.4 ± 0.14 | 16.9 ± 1.67 |
| M + GmFAD3 + AtCb5-A | 2.2 ± 0.25 | 4.6 ± 0.18 | 66.0 ± 2.94 | 50.5 ± 1.82 | 6.0 ± 0.51 | 15.3 ± 0.27 |
| M + GmFAD3 + AtCb5-B | 1.7 ± 0.04 | 5.4 ± 0.49 | 60.5 ± 1.35 | 45.6 ± 3.34 | 11.7 ± 1.21 | 16.5 ± 0.96 |
| M + GmFAD3 + AtCb5-C | 1.3 ± 0.32 | 4.2 ± 0.09 | 69.3 ± 5.35 | 48.8 ± 0.24 | 5.2 ± 1.17 | 19.6 ± 0.06 |
| M + GmFAD3 + AtCb5-E | 2.2 ± 0.05 | 5.8 ± 0.18 | 53.5 ± 0.95 | 36.0 ± 0.84 | 13.3 ± 0.56 | 22.8 ± 0.12 |
| B | | | | | | |
| W + AtFAD3 | 0.8 ± 0.07 | 3.0 ± 0.35 | 79.5 ± 1.15 | 69.3 ± 2.33 | 6.3 ± 0.02 | 0.3 ± 0.01 |
| M + AtFAD3 | 0.7 ± 0.06 | 2.9 ± 0.13 | 78.9 ± 1.40 | 59.2 ± 0.91 | 0.2 ± 0.01 | 0.3 ± 0.03 |
| M + AtFAD3 + GmCb5-A1 | 2.3 ± 0.26 | 5.1 ± 0.51 | 57.4 ± 2.78 | 42.5 ± 2.25 | 10.4 ± 0.70 | 14.0 ± 0.48 |
| M + AtFAD3 + GmCb5-C2 | 1.7 ± 0.08 | 5.6 ± 0.70 | 63.5 ± 0.63 | 53.8 ± 3.57 | 3.9 ± 0.05 | 3.8 ± 0.41 |
| M + AtFAD3 + GmCb5-C3 | 1.7 ± 0.02 | 7.2 ± 0.33 | 64.6 ± 0.45 | 49.4 ± 1.51 | 2.6 ± 0.28 | 2.0 ± 0.10 |

TABLE 8-continued

Fatty Acid composition of yeast co-expressing Cb5 of Arabidopsis (A) or soybean (B) with non-native FAD3 respectively

| | | | | | | | |
|---|---|---|---|---|---|---|---|
| M + AtFAD3 + GmCb5-E1 | 2.5 ± 0.29 | 7.2 ± 0.55 | 45.1 ± 4.33 | 38.5 ± 2.97 | 17.1 ± 2.78 | 13.8 ± 2.58 |

For Cb5 and FAD3 co-expression study 18:2 were added to the culture before induction with galactose. FAMES were analyzed by GC-FID. The induction time for culture maintained at 28° C. and 15° C. were 48 and 96 hour respectively.
Values represents mol percentage of total fatty acids.
± represents SD of three independent cultures.
At = *Arabidopsis thetiana*;
Gm = *Glycine max*;
Cb5 = Cytochrome b5;
W = wild type yeast;
M = mutant yeast disrupted in endogenous Cb5 gene;
ND = Not detected.

Example 5

Retention of Differential ω-3 Desaturation Properties by Cb5 Isoforms

Figure 7:
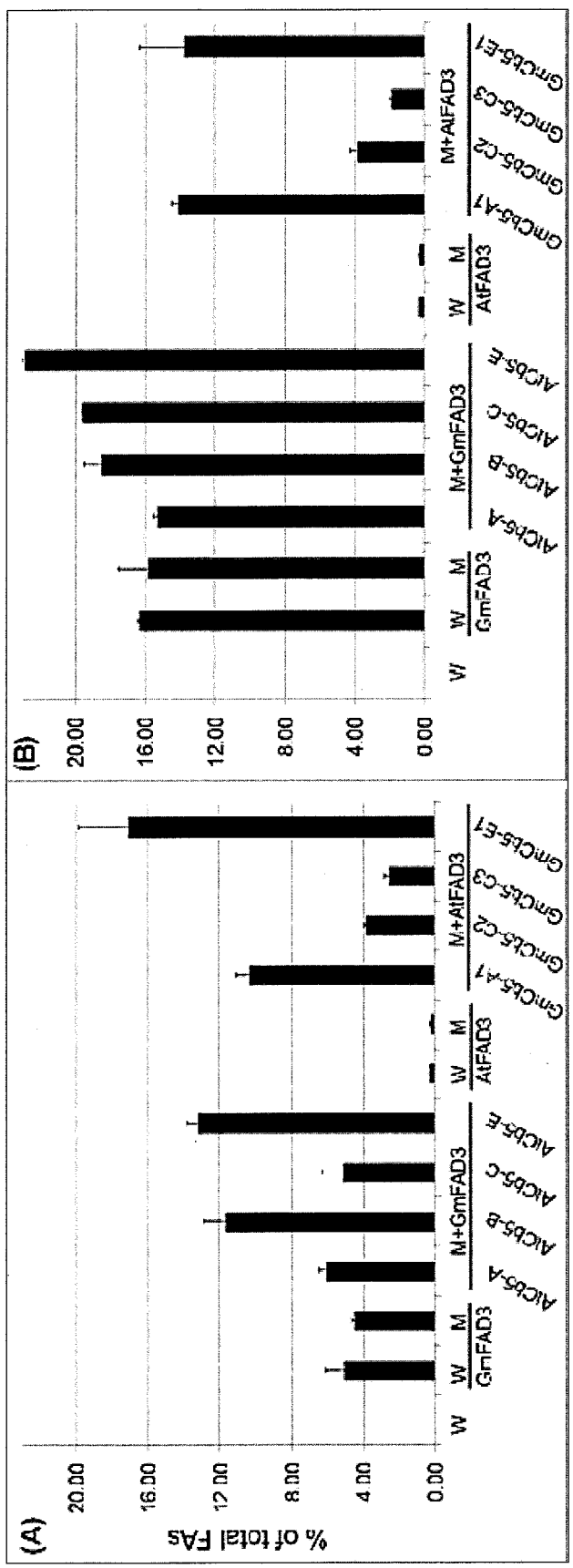
FIG. 7 shows the 18:3 content of yeast co-expressing Cb5 of *Arabidopsis* or soybean and normative FAD3.

Encouraged by demonstration of differential 18:3 accumulation by Cb5 isoforms of both soybean and *Arabidopsis* at comparable growth conditions (FIGS. 5A and 6A), we next explored whether such differential property are retained even under condition of their co-expression with non-native FAD3. To test above, we co-expressed soybean Cb5 (GmCb5) with *Arabidopsis* FAD3 (AtFAD3) and *Arabidopsis* Cb5 (AtCb5) with soybean FAD3 (GmFAD3) individually in mutant cb5 yeast. FIG. 7 shows the result of this study showing the 18:3 content of yeast co-expressing Cb5 of *Arabidopsis* or soybean and non-native FAD3. The experimental conditions were the same as those described in FIG. 5. W=wild type yeast (empty vector pESC control); M=mutant cb5 yeast; Gm=*Glycine max*; At=*Arabidopsis thaliana*. The display of ~3 folds more 18:3 accumulations by AtCb5-B & AtCb5-E compared to both AtCb5-C & AtCb5-A, (FIG. 7A) was reflective of their higher ω-3 desaturation efficiencies as observed with native FAD3 (FIG. 6A). At lower temperature, both AtCb5-E & AtCb5-B were still able to accumulate comparatively more 18:3 than AtCb5-A, but 18:3 level of AtCb5-C became relatively similar to AtCb5-B (FIG. 7B).

On the other hand, retention of higher ω-3 desaturation efficiency associated with GmCb5-A1 and GmCb5-E1 (FIG. 5A) was also observed even under condition with non-native AtFAD3 (FIGS. 7A&B). However, a significant 3-4 fold reduction in 18:3 accumulations in GmCb5-C2 and GmCb5-C3 compared to those observed under condition with native FAD3 (FIG. 5) was quite surprising. The soybean Cb5 & FAD3, (FIG. 5) and GmCb5 & AtFAD3, (FIG. 7) co-expression experiments were performed independently and despite considerable increase in precursor (18:2) in latter experiment, the inability to achieve higher 18:3 accumulation by GmCb5-C2 and GmCb5-C3 indicated their lesser interaction efficiency with AtFAD3.

Example 6

Different Cb5 Isoforms have Different Efficiencies in Modulating Omega-3 Desaturation A mutant yeast strain deficient in its only endogenous microsomal Cb5 gene (also referred to as "mutant cb5 yeast") was used to characterize different Cb5 isoforms from soybean and *Arabidopsis*. Among the four FAD3 genes of soybean, FAD3-1A (Anai et al., 2005) was used, which is similar to FAD3B (Bilyeu et al., 2003). Co-expression of soybean Cb5 genes and the native FAD3 resulted in more than 2 fold increase in 18:3 production in the mutant cb5 yeast as compared to those expressing FAD3 alone. Variations in 18:3 levels were observed among Cb5 isoforms when they were co-expressed with FAD3. The levels of 18:3 accumulation were similar when either Cb5-C2 or Cb5-E1 was co-expressed with FAD3. The levels of 18:3 were about 1.5 fold more when either Cb5-C2 or Cb5-E1 was expressed as compared to those when Cb5-C3 was expressed. The level of 18:3 accumulation when Cb5-A1 was used was greater than that when Cb5-C3 was expressed but lower than those when either Cb5-C2 or Cb5-E1 was expressed.

Similar results were observed when *Arabidopsis* Cb5 and native *Arabidopsis* FAD3 were co-expressed. More specifically, *Arabidopsis* Cb5 and native FAD3 (At2g29980) were co-expressed in the mutant cb5 yeast. Significant increase in 18:3 production was observed in yeast co-expressing *Arabidopsis* Cb5 and FAD3 as compared to those expressing FAD3 alone. Similar to the results obtained using soybean Cb5 isoforms, substantial variation in 18:3 levels among the Cb5 isoforms from *Arabidopsis* was observed. Both Cb5-B & Cb5-E were able to cause accumulation of more 18:3 by 2 to 4 fold than Cb5-A or Cb5-C, respectively.

In order to test whether the effects of these Cb5 isoforms were intrinsic to the Cb5 proteins, the various Cb5 isoforms were co-expressed with a non-native FAD3. In one experiment, soybean Cb5 (GmCb5) was co-expressed with *Arabidopsis* FAD3 (AtFAD3). Retention of higher omega-3 desaturation efficiency associated with GmCb5-A1 or GmCb5-E1 was observed even when each of them was co-expressed with non-native AtFAD3 from *Arabidopsis*. By contrast, a significant 3-4 fold reduction in 18:3 accumulations was observed when GmCb5-C2 or GmGb5-C3 was used, as compared to those observed under the same condition but with native FAD3. The inability of GmCb5-C2 or GmCb5-C3 to achieve higher 18:3 accumulation suggests that they may have less interaction with AtFAD3.

In another experiment, various *Arabidopsis* Cb5 isoforms (AtCb5) were co-expressed with soybean FAD3 (GmFAD3) in the mutant cb5 yeast. AtCb5-B or AtCb5-E showed more 18:3 accumulations by about 3 folds as compared to the levels of 18:3 when either AtCb5-C or AtCb5-A was expressed.

Example 7

Higher Fatty Add Content in the Seeds by Overexpression of *Yarrowia* ATP Citrate Lyase The fungus *Yarrowia lipolytica* possesses the unique capability to accumulate oil in the body, up to about 50% oil on dry weight basis. In order to increase the oil content in seeds of economically valuable crops, the ATP citrate lyase (ACL) genes of *Yarrowia lipolytica* was over-expressed in seed specific manner in *Arabidopsis*.

The *Yarrowia* ATP-citrate lyase (ACL) is encoded by two genes, namely, ACL1 (Genbank: XM_504787) and ACL2 (Genbank:XM_503231). The sequences of ACL1 and ACL2 are shown in FIG. 12. To direct the ACL gene products to the plastids, both genes were engineered to contain an N-terminal plastid transit sequence of coriander desaturase (Cahoon et al., 1992). Two sets of gene cassettes were developed, one with the transit peptide (Construct A) and the other without the transit sequence (Construct B). Because ACL enzymes can catabolite available citrates inside the plastids, overproduction of ACL enzymes in plastids helped boost the synthesis of acetyl CoA. The increased acetyl CoA can be directed toward synthesis of more fatty acids leading to enhanced oil accumulation in the seeds.

Figure 9:
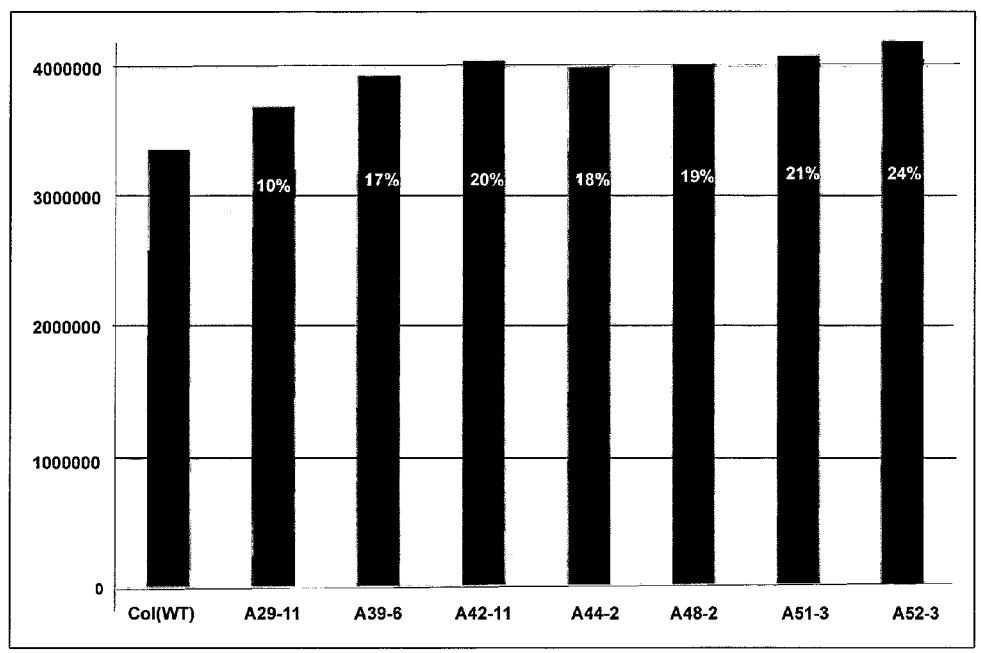
FIG. 9 shows the seed fatty acids area of transgenic *Arabidopsis* over-expressing *Yarrowia* ACL genes.

These gene cassettes were introduced into *Arabidopsis* and the transgenic plants were generated to test the phenotyope, i.e. oil content and components. These transgenic plants were produced to evaluate the hypothesis that these two genes can produce higher levels of seed oil content as compared to the non-transgenic host plant. Preliminary results from seeds of several independent transgenic. *Arabidopsis* lines overexpressing *Yarrowia* ACL1 and ACL2 show an increase of about 10-20% in overall fatty acids in the transgenic lines as compared to the non-transgenic lines (FIG. 9). The % increase in total seed fatty acid for each transgenic line compared to control untransformed Col (WT) is indicated.

The structures of the constructs are shown below. cTP is the transit peptide or plastid localization sequence for directing the Ad gene product to the plastid, which may help increase the acetate/acetyl CoA pool size for de novo fatty acid synthesis.

Construct A—Glycinin:: cTP(cor desat)-YLAcl1+2S Albumin:: cTP (cor dest)-YLAcl2

Construct B—Glycinin:: -YLAcl1+2S Albumin::-YLAcl2

Table 9 shows the distribution of fatty acids in the transgenic and the non transgenic (Columbia) *arabidopsis* seeds. It is recognized that the sample size is relatively small in Table 9; however, it appears that the transgenic plants expressing the YL ACL1 and ACL2 proteins have relatively higher toal oil content as compared to the non-transgenic strains. Moreover, a slight increase in the percentage of unsaturated. FAs such as C18:2 and C18:3 in the transgenic plants are also observed.

TABLE 9

Distribution of fatty acids in the transgenic and the transgenic (Columbia) *arabidopsis* seeds - PRELIMINARY RESULTS

| | Wt-mg | C16:0 | C18:0 | C18:1 | C18:2 | C18:3 | C20:1 | Palmitic acid | Stearic acid | Oleic acid | Linoleic acid | Linoleic acid | Total oil |
|---|---|---|---|---|---|---|---|---|---|---|---|---|---|
| | | | | % Distribution of fatty acids | | | | | mg/g *Arabidopsis* seeds | | | | mg/g |
| Transgenic *arabidopsis* lines developed with the Construct A: | | | | | | | | | | | | | |
| A39-6/2-1 | 1.25 | 9.5 | 3.7 | 17.4 | 34.6 | 18.7 | 16.3 | 18.2 | 7.0 | 31.1 | 60.3 | 33.0 | 149.7 |
| A39-6/2-2 | 1.01 | 9.4 | 3.7 | 17.1 | 34.1 | 19.3 | 16.3 | 20.7 | 8.0 | 34.4 | 67.1 | 38.5 | 168.8 |
| A39-6/2-ave | 1.13 | 9.4 | 3.7 | 17.2 | 34.3 | 19.0 | 16.3 | 19.5 | 7.5 | 32.8 | 63.7 | 35.8 | 159.3 |
| A52-3/1 | 0.98 | 8.7 | 3.5 | 18.0 | 32.9 | 18.6 | 18.2 | 15.3 | 5.3 | 26.8 | 47.4 | 27.0 | 121.8 |
| Au7-2/1-1 | 0.68 | 8.3 | 3.3 | 20.2 | 31.3 | 18.8 | 18.1 | 19.9 | 6.5 | 39.2 | 59.1 | 35.9 | 160.6 |
| Transgenic *arabidopsis* lines developed with the Construct B: | | | | | | | | | | | | | |
| B13-10/2 | 1.01 | 9.2 | 3.4 | 19.9 | 32.8 | 19.3 | 15.4 | 27.9 | 10.7 | 58.0 | 93.1 | 55.6 | 245.3 |
| B6-11/5-1 | 1.12 | 8.5 | 3.0 | 18.2 | 33.0 | 18.8 | 18.4 | 16.0 | 5.2 | 30.0 | 53.1 | 30.6 | 134.8 |
| B6-11/5-2 | 0.97 | 8.5 | 3.2 | 17.9 | 32.7 | 19.0 | 18.7 | 17.4 | 5.9 | 31.6 | 56.4 | 33.1 | 144.4 |
| B6-11/5-ave | 1.04 | 8.5 | 3.1 | 18.1 | 32.9 | 18.9 | 18.6 | 16.7 | 5.5 | 30.8 | 54.8 | 31.8 | 139.6 |
| B7-10/7 | 0.69 | 10.0 | 3.6 | 18.8 | 34.2 | 18.3 | 15.1 | 36.6 | 13.5 | 65.0 | 115.4 | 62.4 | 292.9 |
| Non-transgenic *arabidopsis* Columbia: | | | | | | | | | | | | | |
| Columbia-1 | 0.75 | 8.7 | 3.3 | 23.0 | 30.8 | 16.9 | 17.3 | 15.9 | 4.5 | 32.3 | 41.8 | 23.1 | 117.5 |
| Columbia-2 | 0.98 | 8.8 | 3.4 | 21.7 | 31.2 | 17.4 | 17.4 | 17.5 | 6.2 | 37.6 | 52.5 | 29.6 | 143.4 |
| Columbia-ave | 0.98 | 8.8 | 3.3 | 22.3 | 31.0 | 17.2 | 17.4 | 16.7 | 5.4 | 34.9 | 47.1 | 26.3 | 130.5 |

Analysis with more transgenic lines are in progress
C16:0 Palmitic acid
C18:0 Stearic acid
C18:1 Oleic acid
C18:2 Linoleic acid
C18:3 Linolenic acid
C20:1

Example 8

Generation of Transgenic Plants with Higher Seed Oil Content or More Desirable Fatty Acid Ratio Certain FAD3 genes are overexpressed with certain Cb5 genes in a host plant to achieve higher oil content, and/or to achieve a specifically desirable ratio between different types of fatty acids. Suitable pairs of FAD3-Cb5 may be determined according to Example 1. The FAD 3 and Cb5 genes may be introduced as a transgenes, and more preferably, as a transgene under the control of a seed specific promoter so that the products of the respective transgenes may be expressed in a seed specific manner. Host plants may include but are not limited to soybean, corn, peanut, *Arabidopsis*, etc. Methods for introducing transgenes into a host plant may be found in, for example, in U.S. patent application Ser. Nos. 12/023,237, and 11/684,413, the contents of which are hereby incorporated into this disclosure by reference.

While the foregoing instrumentalities have been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

REFERENCES

In addition to those references that are cited in full in the text, additional information for those abbreviated citations is listed below. The content of all patents, patent applications or other publications cited in this disclosure are incorporated by reference into this disclosure.

1. Napier J A, Sayanova O, Stobart A K, Shewry P R: A new class of cytochrome 115 fusion proteins. Biochem J 1997, 328: 717-720.
2. Smith M A, Jonsson L., Stymne S, Stobart A K: Evidence for cytochrome b5 as electron donor in ricinoleic acid biosynthesis in microsomal preparations from developing castor bean (*Ricinus communis* L.). Biochem J 1992, 287: 141-144,
3, Broadwater J A, Whittle E, Shanklin Desaturation and hydroxylation. Residues 148 and 324 of *Arabidopsis* FAD2, in addition to substrate chain length, exert a major influence in partitioning of catalytic specificity, J Biol Chem 2002, 277: 15613-15620.
4. Kumar R, Wallis J G, Skidmore C, Browse J: A mutation in *Arabidopsis* cytochrome b5 reductase identified by high throughput screening differentially affects hydroxylation and desaturation. Plant J 2006, 48: 920-932.
5, Cahoon E B, Ripp K G, Hall S E, Kinney A J: Formation of conjugated AΔ8, Δ10-double bonds by Δ12-oleic-acid desaturase related enzymes. J Biol Chem 2001, 276: 2637-2643.
6, Cahoon E B, Dietrich C R, Meyer K, Darnude H, Dyer J M, Kinney A J: Conjugated fatty acids accumulate to high levels in phospholipids of metabolically engineered soybean and *Arabidopsis* seeds, Phytochemistry 2006, 67: 1166-1176.
7, Nam J W, Kappock T J: Cloning and transcriptional analysis of Crepis alpine fatty acid desaturases affecting the biosynthesis of crepenynic acid. J Exp Bot 2007, 58: 1421-32,
8. Napier J A, Michaelson L V, Sayanova 0: The role of cytochrome b5 fusion desaturases in the synthesis of polyunsaturated fatty acids. Prosta Leukot Essent FAs 2003, 68: 135-143.
9. Nagano M, Ihara-Ohori Y, Imai H, Inada N, Fujimoto M, Tsutsumi N, Uchimiya H, Kawai-Yamada M: Functional association of cell death suppressor, *Arabidopsis* Bax inhibitor-1, with fatty acid 2-hydroxylation through cytochrome b5. Plant J 2009, 58: 122-134,
10. Rahier A, Smith M, Taton M: The role of cytochrome b5 in 4α-methyl-oxidation and C5(6) desaturation of plant sterol precursors. Biochem Biophys Res Commun 1997, 236: 434-437.
11. de Vetten N, ter Horst J, van Schaik H P, de Boer A, Mol J. Koes R: A cytochrome b5 is required for full activity of flavonoid 3',5'-hydroxylase a cytochrome P450 involved in the formation of blue flower colors. PNAS 1999, 96: 778-783.
12. Fan R C, Peng C C, Xu Y H, Wang X F, Li V. Shang Y, Du S V, Zhao R, Zhang X V, Zhang L Y, and Zhang D P: Apple sucrose transporter SUT1 and sorbitol transporter SOT6 interact with Cytochrome b5 to regulate their affinity for substrate sugars, Plant Physiol 2009 150:1880-1901.
13. Ohlrogge J, Browse J: Lipid biosynthesis. Plant Cell 1995, 7: 957-970.
14. Browse J, Somerville C: Glycerolipid synthesis: biochemistry and regulation. Arum Rev Plant Physiol Plant Mol Biol 1991, 42: 467-506.
15. Miguel M, Browse J: *Arabidopsis* mutants deficient in polyunsaturated fatty acid synthesis. Biochemical and genetic characterization of a plant oleoyl-phosphatidyleholine desaturase, J Biol Chem 1992, 267: 1502-1509.
16. Smith M A, Stobart A K, Shewry P R, Napier J A: Tobacco cytochrome b5: cDNA isolation, expression analysis and in vitro protein targeting. Plant Mol Biol 1994, 25: 527-537
17. Napier J A, Smith M A, Stobart A K, Shewry P R: Isolation of a cDNA encoding a cytochrome b5 specifically expressed in developing tobacco seeds. Planta 1995, 197: 200-202.
18. Fukuchi-Mizutani M, Mizutani M. Tanaka Y, Kusumi T, Ohta D: Microsomal electron transfer in higher plants: cloning and heterologous expression of NADH-cytochrome b5 reductase from *Arabidopsis*. Plant Physiol 1999, 119: 353-362.
19. Hwang V T, Pelitire S M, Henderson M P, Andrews D W, Dyer J M, Mullen R T: Novel targeting signals mediate the sorting of different isoforms of the tail-anchored membrane protein cytochrome b5 to either endoplasmic reticulum or mitochondria. Plant Cell 2004, 16: 3002-3019.
20. Altuve A, Wang L, Benson D R, Rivera M: Mammalian mitochondrial and microsomal cytochromes b5 exhibit divergent structural and biophysical Characteristics. Biochem Biophys Res Commun 2004, 314: 602-609.
21. Mitchell A G, Martin C E: A novel cytochrome b5-like domain is linked to the carboxyl terminus of the *Saccharomyces cerevisiae* Δ-9 fatty acid desaturase. J Biol Chem 1995, 270: 29766-29772.
22. Sayanova O, Smith M A, Lapinskas P, Stobart A K, Dobson G, Christie W W, Shewry P R, Napier J A: Expression of a borage desaturase cDNA containing an N-terminal cytochrome b5 domain results in the accumulation of high levels of Δ6-desaturated fatty acids in transgenic tobacco. PNAS 1997, 94: 4211-1216.
23. Lu G, Lindqvist Y, Schneider G, Dwivedi U, Campbell W: Structural studies on corn nitrate reductase: refined structure of the cytochrome b reductase fragment at 2.5 A°, its ADP complex and an active-site mutant and modeling of the cytochrome b domain. J Mol Biol 1995, 248: 931-948.
24. Covello P S, Reed D W: Functional expression of the extraplastidial *Arabidopsis thaliana* oleate desaturase gene (Fad2) in *Saccharomyces cerevisiae*. Plant Physiol 1996, 111: 223-226.
25. Reed E W, Schafer L A, Covello P S: Characterization of the *Brassica* napes extraplastidial linoleate desaturase by expression in *Saccharomyces cerevisiae*. Plant Physiol 2000, 122: 715-720.

26. Dyer J M, Chapital D C, Cary J W, Pepperman A B: Chilling-sensitive, post-transcriptional regulation of a plant fatty acid desaturase expressed in yeast. Biochem Biophys Res Common 2001, 282: 1019-1025, 27. Vrinten P, Z, Munchinsky M A, Rowland G, Qiu X: Two FAD3 desaturase genes control the level of linolenic acid in flax seed. Plant Physiol 2005, 139: 79-87.

28. Dyer J M, Chapital D C, Kuan J C, Mullen R1, Turner C, McKeon T A, Pepperman A B: Molecular analysis of a bifunctional fatty acid conjugase/desaturase from tung. Implications for the evolution of plant fatty acid diversity. Plant Physiol 2002, 130: 2027-38.

29. Smith M A, Moon H, Chowrira G, Kunst L: Heterologous expression of a fatty acid hydroxylase gene in developing seeds of Arabidopsis thaliana. Planta 2003, 217: 507-516.

30. Shockey J M, Dhanoa P K, Dupuy T, Chapital D C, Mullen. R T, Dyer J M: Cloning, functional analysis, and subcellular localization of two isoforms of NADH:cytochrome b5 reductase from developing seeds of tong (Vernicia fordii). Plant Sci 2005, 169: 375-385.

31 Maggio C. Barbante A, Ferro F, Frigerio L, Pedrazzini E: Intracellular sorting of the tail-anchored protein cytochrome b5 in plants: a comparative study using different isoforms from rabbit and Arabidopsis. J Exp Rot 2007, 58: 1365-1379.

32. Shoemaker R P, Keim L, Vodkin E, Retzel S W et al: A compilation of soybean EST's: generation and analysis. Genome 2002, 45: 329-338.

33, Shoemaker R C, Schlueter J, Doyle J J: Paleopolyploidy and gene duplication in soybean and other legumes. Curr Opin Plant Biol 2006, 9: 104-109

34. Tang G Q, Novitzky W P, Griffin H C, Huber S C, Dewey R E: Oleate desaturase enzymes of soybean: evidence of regulation through differential stability and phosphorylation. Plant J 2005, 44: 433-446.

35. Petrini G A, Altabe S G, Uttaro A D: *Trypanosoma brucei* oleate desaturase may use a cytochrome b5-like domain in another desaturase as an electron donor. Eur J Biochem 2004, 271: 1079-1086, 36. Broun P, Shanklin J, Whittle E, Somerville C: Catalytic plasticity of fatty acid modification enzymes underlying chemical diversity of plant lipids. Science 1998, 282: 1315-1317.

37, Pedrazzini E: Tail-anchored proteins in plants, J Plant Biol 2009, 52: 88-101.

38. Kaziwara S. Shirai A, Fujii T, Toguri T, Nakamura K, Obtaguchi K: Polyunsaturated fatty acid biosynthesis in *Saccharomyces cerevisiae*: Expression of ethanol tolerance and the FAD2 gene from *Arabidopsis thaliana*, Appl Env Microbial 1996, 62: 4309-4313.

39, Anai T, Yamada T, Kinoshita T, Rahman S M, Takagi Y: identification of corresponding genes for three low-α-linolenic acid mutants and elucidation of their contribution to fatty acid biosynthesis in soybean seed Plant Science 2005, 168: 1615-1623.

40, Bilyeu K D, Palavalli L, Sleper D A, Beuselinck P R: Three microsomal omega-3 Fatty-acid desaturase genes contribute to soybean linolenic acid levels Crop Sci 2003, 43: 1833-1838.

41. Smith M A, Cross A R, Jones O T, Griffiths W T, Stymne 5, Stobart K: Electron-transport components of the 1-acyl-2-oleoyl-sn-glycero-3-phosphocholine Δ12-desaturase (Δ12-desaturase) in microsomal preparations from developing safflower (*Carthamus tinctorius* L.) cotyledons. Biochem J 1990, 272: 23-29.

42. Dyer J M, Mullen R T: Engineering plant oils as high-value industrial feedstocks for biorefining: the need for underpinning cell biology research, Physiol Plant 2008, 132: 11-22.

43. Sambrook J, Fritsch E F, Maniatis T: Molecular Cloning: A laboratory manual, 2nd edn. 1989, New York: Cold Spring Harbor Laboratory Press.

44. Aguilar F, Montandon P E, Stutz E: Two genes encoding the soybean translation elongation factor eEF-1 alpha are transcribed in seedling leaves. Plant Mol Biol 1991, 17: 351-360, 45. Larkin M A, Blackshields G, Brown N P, Chema R, MeGettigan P A, McWilliam H, Valentin F, Wallace I M, Wilm A, Lopez R, Thompson J D, Gibson, T J, Higgins D G: Clustal W and Clustal X version 2.0. Bioinformatics 2007, 23:2947-2948.

46. Tamura K, Dudley J, Nei M, Kumar S: MEGA4: Molecular evolutionary genetics analysis (MEGA) software version 4.0. Mol Biol Evolution 2007, 24: 1596-1599.

47. Rangasamy and Ratledge (2000) Genetic Enhancement of Fatty Acid Synthesis by Targeting Rat Liver ATP:Citrate Lyase into Plastids of Tobacco. Plant Physiology, 122: 1231-38.

48. Cahoon et al. (1992) Expression of a coriander desaturase results in petroselinic acid production in transgenic tobacco. PNAS, 89:11184-88.

49. Cahoon, E B (2003) Genetic Enhancement of Soybean Oil for Industrial Uses: Prospects and Challenges. AgBioForum, 6(1&2): 11-13.

50. Damude et al., (2006) Identification of bifunctional deltal 2/omega-3 fatty acid desaturases for improving the ratio of omega3 to omega6 fatty acids in microbes and plants. PNAS, 103: 9446-9451.

51. Anal T et al., (2005) identification of corresponding genes for three low-α-linolenic acid mutants and elucidation of their contribution to fatty acid biosynthesis in soybean seed. Plant Science, 168: 1615-1623.

52. Bilyeu K D et al., (2003) Three microsomal omega-3 Fatty-acid desaturase genes contribute to soybean linolenic acid levels. Crop Sd, 43: 1833-1838.

53. Simopoulos, Artemis P (1999) Essential fatty acids in health and chronic disease. Am J Clin Nutr; 70(suppl): 560S-9S.

54. Simopoulos, Artemis p (2008) The importance of the Omega-6/Omega-3 Fatty Acid Ratio in Cardiovascular Disease and Other Chronic Diseases. Exp Biol Med (Maywood);233(6):674-88.

We claim:

1. A method for generating a transgenic plant, said method comprising the steps of:
   a) introducing a first transgene into a host plant, said first transgene is at least 95% identical to the sequence of a polynucleotide selected from the group consisting of SEQ ID NOs:1, 2, and 4;
   b) introducing a second transgene encoding a fatty acid desaturase is introduced into said host plant; and
   c) allowing said host plant to express a protein encoded by said first transgene.

2. The method of claim 1, wherein said transgenic plant produces higher oil content than the non-transgenic host plant prior to transfection with the first and second transgenes.

3. The method of claim 1, wherein the fatty acids produced by said transgenic plant have higher percentage of unsaturated fatty acids than the fatty acids produced by the non-transgenic host plant.

4. The method of claim 1, wherein the plant is selected from the group consisting of soybean, *Arabidopsis*, corn, peanut and canola.

5. The method of claim 1, wherein said second transgene is selected from the group consisting of FAD2 and FAD3 from a higher plant.

6. The method of claim 1, wherein said first and second transgenes are from the same plant species.

7. The method of claim 1, wherein said first and second transgenes are from different plant species.

8. A transgenic plant generated from a host plant according to the method of claim 1.

* * * * *

SEQUENCE LISTING

```
<160> NUMBER OF SEQ ID NOS: 61

<210> SEQ ID NO 1
<211> LENGTH: 405
<212> TYPE: DNA
<213> ORGANISM: Glycine max
```

<400> SEQUENCE: 1

```
atggcttcag atcggaaact tcacactttt gaggaggtgg caaagcacaa ccagaccaag      60
gattgctggc tcatcatttc tggcaaggtg tatgatgtca cccctttcat ggaggatcat     120
cccggaggtg atgaggtttt gttatctgca acagggaaag atgcaaccaa tgactttgaa     180
gatgtggggc acagtgattc tgctagagat atgatgaaaa atactacat tggtgagatt      240 gatgcatcaa ccgtcccact aaaacggacc tacattccac ctcagcaagc tcagtacaat     300
cctgataaga ctccagaatt tgtgatcaag atttttgcagt tcctggtccc tctcctgatc    360
ttgggcttgg cctttgttgt gcgacactac accaagaaag agtag                     405
```

<210> SEQ ID NO 2
<211> LENGTH: 441
<212> TYPE: DNA
<213> ORGANISM: Glycine max

<400> SEQUENCE: 2

```
atgggttcaa aaccaagac ttttaccttt gaagaggtgg ctaaacacaa tcacaggaag       60
gattgttgga ttatagtcaa agggaaggtg tatgatgtca ccccatttt ggatgatcat      120 ccaggaggtg atgaagtttt agtgactgca acagagaagg atgccaccac tgattttgaa     180
gatattggcc acagtgattc agcaacacag atgatgaaaa atactttgt tggggaggtt      240 gacaccaaca ctcttccagc acaagttacc agcaacaaca gtgtacgcca accaacacaa     300
gcaccacctg cctataacaa tcaatcttca ggatttgttg tgaagatgtt gcagtacata     360
gtgccattgc tgatattggc cttcattt ggcctgcagt actatggcaa aaaaaacaag       420
tccactgagt cagaaaattg a                                               441
```

<210> SEQ ID NO 3
<211> LENGTH: 426
<212> TYPE: DNA
<213> ORGANISM: Glycine max

<400> SEQUENCE: 3

```
atggcctcaa atcccaaaac tttgaccttt gaggaggtag ctaagcacaa caacaaaaag      60
gattgctgga ttattatcaa tggaaaggtg tatgatatca caccattttt ggatgagcat     120
ccaggaggtg atgaagtttt gctgacgtca acagggaagg atgccaccat tgattttgaa     180
gatgtgggcc acagtgattc tgctatagaa atgatgaaaa atacttcat tgggaaggtt      240 gacacttcca ctcttccacc caaagttagc catagtctgc acaacctac acaaacacat      300 ggcgctggca atcaatcttc tggatttgtt gtaaagatct tgcaattcct gttgccattg     360
ttgatactgg gcctcgcatt tgccctgcag tattatggcc aaaagaagca tgctagcacc     420
tcatga                                                                426
```

<210> SEQ ID NO 4
<211> LENGTH: 408
<212> TYPE: DNA
<213> ORGANISM: Glycine max

<400> SEQUENCE: 4

```
atgggtgggg agcggaacaa ggtcttctct ttggccgagg tctctcagca caacaatgcc      60
aaagactgtt ggcttgtcat tcatggcaag gtttataatg tgacaaagtt cttggaggac     120
caccctggag gggatgaggt cctgttgtct tccacaggga agatgcaac caatgatttt      180 gaggatattg gtcacagcac cagcgccgta gccatgatgg atgagttcta tgttggagac     240
```

-continued

| | |
|---|---|
| attgatacat caaccatccc cagcaaggtt aagtacactc ctccaaaaca acctcactat | 300 |
| aaccaggaca agatgccgga gttcatcatc aggatcctcc agtttctagt tcccttgttt | 360 |
| atcttgggtt tggcagttgg tattcgtttc tacaccaaat caacataa | 408 |

<210> SEQ ID NO 5
<211> LENGTH: 405
<212> TYPE: DNA
<213> ORGANISM: Arabidopsis thaliana

<400> SEQUENCE: 5

| | |
|---|---|
| atgtcttcag atcggaaggt tctaagtttt gaagaagttt caaagcacaa caaaactaag | 60 |
| gattgttggc ttattatttc cggcaaggtg tatgatgtga ctccattcat ggatgatcat | 120 |
| cctggaggcg atgaagtctt gttgtcctca acagggaaag atgctacaaa tgattttgaa | 180 |
| gacgttggtc acagcgacac tgcaagggac atgatggaca aatatttcat tggtgagatt | 240 |
| gattcgtcta gtgttccagc aactaggaca tacgttgcac cacagcaacc agcctacaac | 300 |
| caagacaaga caccagaatt cattatcaag attcttcagt tccttgttcc gatcttgatc | 360 |
| ttgggattgg ctcttgtcgt ccgtcactat accaagaaag actag | 405 |

<210> SEQ ID NO 6
<211> LENGTH: 423
<212> TYPE: DNA
<213> ORGANISM: Arabidopsis thaliana

<400> SEQUENCE: 6

| | |
|---|---|
| atgggcggag acggaaaagt tttcaccttg tccgaggttt ctcagcacag tagcgccaag | 60 |
| gattgttgga tcgtcatcga cggcaaggtt tatgatgtga caaagttctt ggatgatcat | 120 |
| cctggtggtg atgaggttat cttgacttct acagggaaag atgcgaccga tgatttcgag | 180 |
| gatgtgggac atagttcgac tgcgaaagcc atgctagatg agtactatgt gggtgatatt | 240 |
| gacacagcta ctgtgccggt taaagctaag tttgtgcctc ctacgtcgac gaaagccgtg | 300 |
| gctactcagg ataagagctc ggattttgtt attaagctcc ttcagttcct tgttccactt | 360 |
| ctaatcttag gcttggcttt cggcattcgg tactacacta agaccaaggc tccttcttct | 420 |
| tga | 423 |

<210> SEQ ID NO 7
<211> LENGTH: 399
<212> TYPE: DNA
<213> ORGANISM: Arabidopsis thaliana

<400> SEQUENCE: 7

| | |
|---|---|
| atggcgaatc taatttcgtt tcacgatgtg gctaaacata agtgcaagaa cgattgttgg | 60 |
| attctcatcc atggaaaggt ctatgacatc agcactttca tggacgaaca tcccggaggt | 120 |
| gacaatgttc tcctcgccgt caccgggaaa gacgcgtcga tcgatttcga agatgtgaac | 180 |
| catagcaaag atgccaagga gctaatgaag aaatactgta tcggtgacgt tgaccagtca | 240 |
| acggttccgg tgacgcaaca gtatattccg ccgtgggaga aggaatctac ggcggcggaa | 300 |
| acaactaaag aagaatctgg aaagaagctg cttatctact taattcctct cttgatactc | 360 |
| ggcgttgctt tcgctctcag attctacaac aacaagtag | 399 |

<210> SEQ ID NO 8
<211> LENGTH: 405
<212> TYPE: DNA
<213> ORGANISM: Arabidopsis thaliana

```
<400> SEQUENCE: 8
atgggagacg aagcaaagat cttcactctt tcagaagttt cagagcataa tcaagctcat      60
gactgttgga ttgtcatcaa tggaaaggtg tacaatgtga ccaagtttct tgaagaccat     120
ccaggtgggg acgatgttct cttgtcttca acaggtaagg atgcaacgga tgattttgag     180
gacgtgggtc acagcgagag tgcaagagaa atgatggagc agtactacgt aggagagatt     240
gatccaacaa caataccaaa gaaagtcaaa tacacacctc taaacagcc tcactacaat      300 caagacaaga cctctgaatt cataatcaag ctccctccagt tcctcgtacc ccttgccatt    360
cttggtttag cagtcggaat ccgtatctac accaaatcag ggtag                     405

<210> SEQ ID NO 9
<211> LENGTH: 1953
<212> TYPE: DNA
<213> ORGANISM: Yarrowia lipolytica

<400> SEQUENCE: 9
atgtctgcca acgagaacat ctcccgattc gacgcccctg tgggcaagga gcaccccgcc      60
tacgagctct tccataacca cacgatctc ttcgtctatg gtctccagcc tcgagcctgc     120
cagggtatgc tggacttcga cttcatctgt aagcgagaga acccctccgt ggccggtgtc     180
atctatccct cggcggcca gttcgtcacc aagatgtact ggggcaccaa ggagactctt     240
ctccctgtct accagcaggt cgagaaggcc gctgccaagc accccgaggt cgatgtcgtg     300
gtcaactttg cctcctctcg atccgtctac tcctctacca tggagctgct cgagtacccc     360
cagttccgaa ccatcgccat tattgccgag ggtgtccccg agcgacgagc ccgagagatc     420
ctccacaagg cccagaagaa gggtgtgacc atcattggtc ccgctaccgt cggaggtatc     480
aagcccggtt gcttcaaggt tggaaacacc ggaggtatga tggacaacat tgtcgcctcc     540
aagctctacc gacccggctc cgttgcctac gtctccaagt ccggaggaat gtccaacgag     600
ctgaacaaca ttatctctca caccaccgac ggtgtctacg agggtattgc tattggtggt     660
gaccgatacc tggtactac cttcattgac catatcctgc gatacgaggc cgaccccaag     720
tgtaagatca tcgtcctcct tggtgaggtt ggtggtgttg aggagtaccg agtcatcgag     780
gctgttaaga acggccagat caagaagccc atcgtcgctt gggccattgg tacttgtgcc     840
tccatgttca agactgaggt tcagttcggc cacgccggct ccatggccaa ctccgacctg     900
gagactgcca aggctaagaa cgccgccatg aagtctgctg gcttctacgt ccccgatacc     960
ttcgaggaca tgcccgaggt ccttgccgag ctctacgaga gatggtcgc caagggcgag    1020 ctgtctcgaa tctctgagcc tgaggtcccc aagatcccca ttgactactc ttgggcccag    1080
gagcttggtc ttatccgaaa gcccgctgct ttcatctcca ctatttccga tgaccgaggc    1140
caggagcttc tgtacgctgg catgcccatt tccgaggttt tcaaggagga cattggtatc    1200
ggcggtgtca tgtctctgct gtggttccga cgacgactcc ccgactacgc ctccaagttt    1260
cttgagatgg ttctcatgct tactgctgac cacggtcccg ccgtatccgg tgccatgaac    1320
accattatca ccacccgagc tggtaaggat ctcatttctt ccctggttgc tggtctcctg    1380
accattggta cccgattcgg aggtgctctt gacggtgctg ccaccgagtt caccactgcc    1440
tacgacaagg tctgtcccc ccgacagttc gttgatacca tgcgaaagca gaacaagctg    1500
attcctggta ttggccatcg agtcaagtct cgaaacaacc ccgatttccg agtcgagctt    1560
gtcaaggact tgttaagaa gaacttcccc tccacccagc tgctcgacta cgcccttgct    1620
gtcgaggagg tcaccaccctc caagaaggac aacctgattc tgaacgttga cggtgctatt    1680
```

```
gctgtttctt tgtcgatct catgcgatct tgcggtgcct ttactgtgga ggagactgag      1740
gactacctca agaacggtgt tctcaacggt ctgttcgttc tcggtcgatc cattggtctc      1800
attgcccacc atctcgatca gaagcgactc aagaccggtc tgtaccgaca tccttgggac      1860
gatatcacct acctggttgg ccaggaggct atccagaaga agcgagtcga gatcagcgcc      1920
ggcgacgttt ccaaggccaa gactcgatca tag                                  1953
```

<210> SEQ ID NO 10
<211> LENGTH: 1494
<212> TYPE: DNA
<213> ORGANISM: Yarrowia lipolytica

<400> SEQUENCE: 10

```
atgtcagcga aatccattca cgaggccgac ggcaaggccc tgctcgcaca ctttctgtcc       60
aaggcgcccg tgtgggccga gcagcagccc atcaacacgt tgaaatggg cacacccaag      120 ctggcgtctc tgacgttcga ggacggcgtg ccccccgagc agatcttcgc cgccgctgaa      180
aagacctacc cctggctgct ggagtccggc gccaagtttg tggccaagcc cgaccagctc      240
atcaagcgac gaggcaaggc cggcctgctg gtactcaaca gtcgtgggag ggagtgcaag      300
ccctggatcg ccgagcgggc cgccaagccc atcaacgtgg agggcattga cggagtgctg      360
cgaacgttcc tggtcgagcc cttttgtgcc cacgaccaga agcacgagta ctacatcaac      420
atccactccg tgcgagaggg cgactggatc ctcttctacc acgagggagg agtcgacgtc      480
ggcgacgtgg acgccaaggc cgccaagatc ctcatcccg ttgacattga gaacgagtac       540
ccctccaacg ccacgctcac caaggagctg ctggcacacg tgcccgagga ccagcaccag      600
accctgctcg acttcatcaa ccggctctac gccgtctacg tcgatctgca gtttacgtat      660
ctggagatca accccctggt cgtgatcccc accgccagg gcgtcgaggt ccactacctg       720
gatcttgccg gcaagctcga ccagaccgca gagtttgagt gcggcccaa gtgggctgct       780 gcgcggtccc ccgccgctct gggccaggtc gtcaccattg acgccggctc caccaaggtg      840
tccatcgacg ccggccccgc catggtcttc cccgctcctt tcggtcgaga gctgtccaag      900
gaggaggcgt acattgcgga gctcgattcc aagaccggag cttctctgaa gctgactgtt      960
ctcaatgcca agggccgaat ctggaccctt gtggctggtg gaggagcctc cgtcgtctac     1020
gccgacgcca ttgcgtctgc cggctttgct gacgagctcg ccaactacgg cgagtactct     1080
ggcgctccca acgagaccca gacctacgag tacgccaaaa ccgtactgga tctcatgacc     1140
cggggcgacg ctcaccccga gggcaaggta ctgttcattg gcggaggaat cgccaacttc     1200
acccaggttg gatccacctt caagggcatc atccgggcct ccgggactag ccagtcttct     1260
ctgcacaacc acaaggtgaa gatttacgtg cgacgaggcg gtcccaactg gcaggagggt     1320
ctgcggttga tcaagtcggc tggcgacgag ctgaatctgc catggagat ttacggcccc      1380 gacatgcacg tgtcgggtat tgttcctttg gctctgcttg gaaagcggcc caagaatgtc     1440
aagccttttg gcaccggacc ttctactgag gcttccactc ctctcggagt ttaa           1494
```

<210> SEQ ID NO 11
<211> LENGTH: 405
<212> TYPE: DNA
<213> ORGANISM: Glycine max

<400> SEQUENCE: 11

```
atggcttcag atcggaaact tcacactttc gaggaggtgg caaagcacga ccagaccaag       60
gattgctggc tcatcatttc tggcaaggtg tatgatgtca cccctttcat ggaggatcat      120
```

```
cccggaggtg atgaggtttt gttatctgca acagggaaag atgcaaccaa tgattttgaa    180
gatgttggac acagtgattc tgctagagat atgatggaaa aatactacat tggtgagatt    240
gattcatcaa ctgtaccact aaaacgtacc tacattccac ctcagcaagc tcagtacaat    300
cctgacaaga ctccagaatt tgtgatcaag attttgcagt tcctggtccc tctcctgatc    360
ttgggcttgg cctttgttgt gcgacactac accaagaaag agtag                    405
```

<210> SEQ ID NO 12  
<211> LENGTH: 429  
<212> TYPE: DNA  
<213> ORGANISM: Glycine max
<400> SEQUENCE: 12

```
atggatgagg agcgcaaggt atacactttg gcccaagtat ctgagcacaa cacctccaaa     60
gattgctggc tcataattga tggcaaggtt tacaatgtca caagtttctt agatgatcat    120
cctggtgggg atgatgtctt ggtgtcttcc acagggaaag atgccactga tgactttgag    180
gatgttggtc acagtaaagg tgctagagcc atgttggatg atttatatat tggagacatt    240
gatccatcaa ccatccctac caaggttcag aacactcctc aacacaaacc tcaaaataat    300
caggacaaga catcatcatc gtcatcatca tcatcagact tcatgaccaa gatgctccag    360
tttctacttc ccctgcttat cttgggtgtt gcggttggta ttcgtttcta acaccaaa     420 tcaacatag                                                            429
```

<210> SEQ ID NO 13  
<211> LENGTH: 417  
<212> TYPE: DNA  
<213> ORGANISM: Glycine max
<400> SEQUENCE: 13

```
atgggtgggg agcgcaaggt ttacactttg gccgaagtat ctgagcacaa cacatccaaa     60
gattgctggc tcatcattga tggcaaggtt tataatgtca caaaattctt agatgaccat    120
cctggtgggg atgatgtctt gttgtcttcc acagggaaag acgccactga tgactttgag    180
gatgttggtc acagtaaagg tgctagagcc atgttggatg atttatatgt tggagacatt    240
gatccatcaa ccatccctac caaggttcag cacactcctc taacacaacc tcaaaataat    300
caggacaaga catcatcatc atcagactcc atgaccaaga tgctccagtt tctacttccc    360
ctgcttatct gggtgttgc ggttggtatt cgtttctaca acccaaatc tacatag       417
```

<210> SEQ ID NO 14  
<211> LENGTH: 408  
<212> TYPE: DNA  
<213> ORGANISM: Glycine max
<400> SEQUENCE: 14

```
atgggtgggg agcgcaacaa ggtcttcact ttggccgagg tctctcagca caacaatgcc     60
aaagactgtt ggcttgtcat tcatggcaag gtttataatg taacaaagtt tttggaagat    120
caccctggtg gggatgaggt cctgttgtct tccacaggga agatgcaac caatgatttt    180 gaggatattg gtcacagcac cagtgccgta gccatgatgg atgagttcta tgttggagac    240
attgatacat caaccatccc cagcaaggtt aagtacactc tccaaaaaca acctcactat    300
aaccaggaca agactccgga gttcatcata aggatcctcc agtttctagt ccgttgtttt    360
atcttgggtt tggcagttgg cattcgtttc tacaccaaat caacatga                408
```

```
<210> SEQ ID NO 15
<211> LENGTH: 429
<212> TYPE: DNA
<213> ORGANISM: Glycine max

<400> SEQUENCE: 15
atgggttcaa aaaccaagac ttttaccttt gaggaggtgg ctaagcacaa tcacaggaag      60
gattgctgga ttatagtcaa agggaaggtg tatgatgtca ccccattttt ggatgatcat     120
ccaggaggtg atgaagtttt agtgactgca acagagaagg atgccaccac tgattttgaa     180
gatattgggc acagtgattc agcaacagag atgatggaaa atactttgt tggtgaggtt      240 gacaccaaca ctcttccagc acaagttacc agcagcagca gtgtacgccc accaacacaa     300
gcacctgtct ataacaatca atcttctgga tttgttgtga agatcttgca gtacatagtg     360
ccattgctga tattggcctt tgcatttggc ctgcagtact atggcaaaaa aagcaagtca     420
gaaaattga                                                            429

<210> SEQ ID NO 16
<211> LENGTH: 426
<212> TYPE: DNA
<213> ORGANISM: Glycine max

<400> SEQUENCE: 16
atggcttcaa atcccaaacc tttgactttt gaggaggtgg ctaatcacaa caacaaaaag      60
gattgctgga ttattatcaa tggaaaggtg tatgatatca cgccatttct ggatgagcat     120
cctggaggag atgaagtttt ggtaacgtca acagggaagg atgccaccat tgattttgaa     180
gatgtgggcc acagtgattc tgccatagaa atgatggaaa atacttcgt cgggaaggtt      240 gacacttcca ctcttccagc gaaagttaac catagtctgc acaacctac acaagcaggt      300 ggcgctggca atcaatcttc tggatttgtt gtaaagatct gcaattcct gttgccattc      360 ttgatattgg ccttgccttt gccctgcag tactatggca aaaagaagca tgctagcacc      420
tcatga                                                               426

<210> SEQ ID NO 17
<211> LENGTH: 366
<212> TYPE: DNA
<213> ORGANISM: Glycine max

<400> SEQUENCE: 17
atgccaaccc tcaccaattt ctactccatc aaagatttat cccagcacac taccaaagac      60
gattgctgga tcctcgttga tggaaaggta tacgacgtga cacagtattt ggatgatcat     120
cccggtggag atgatgtaat cctcgccgca accgggaaag acgcaacaga agaatttgaa     180
gatgctggcc acagcaaaag tgctagagaa catatggagc agtattgtat tggtgagctt     240
gacacatctt ctccaatttc caccaaagaa aagttcatac aactcactaa gcaatattgg     300
gttgttccgg caaccgtcgt cggtatctcg gtggtagtag cttctcttata cttacgtaag    360 aagtag                                                               366

<210> SEQ ID NO 18
<211> LENGTH: 691
<212> TYPE: DNA
<213> ORGANISM: Vernicia fordii

<400> SEQUENCE: 18
tgacaaacaa cagtgagatt aaagtcttag accttacctt ccttctctgg gagactatta      60
gaggggaaaa aggatggctt cagatcccaa aattcacaaa tttgaagatg ttaaagtgca     120
```

| | |
|---|---|
| caacaaaatt aaggattgtt ggctcattat ctctggcaag gtgtatgatg taacccccatt | 180 |
| catggaagac catcctggag gagatgaagt cttgctgtca tcaactggaa aagatgcaac | 240 |
| aaatgatttt gaagatgtgg gtcacagtga ttctgctaga gacatgatgg aaaaatacta | 300 |
| tattggtgaa atagattcat ccactgttcc agcaaatcgg acacacatcc ctccgaagca | 360 |
| agtctacaat caggacaaga gctcagagtt cttcattaag atcttgcagt ttctcgttcc | 420 |
| tctcttgatc ttaggcttag cctttgcggt ccgacacttc accaagaaag agtaggctaa | 480 |
| ttacatgtag gtcccttttt gaagggttta attgtggact gtacaactta aattttcaaa | 540 |
| gggttttttt tttttttttt tttttcttct tgcagtgtct tgatgtctgg gaaccatggt | 600 |
| gtctgggaat gtatttggaa cacaatgttt gccttgttgg atgataattg aaaagcagga | 660 |
| taatgttccc tttcttgcca aaaaaaaaaa a | 691 |

<210> SEQ ID NO 19
<211> LENGTH: 705
<212> TYPE: DNA
<213> ORGANISM: Vernicia fordii

<400> SEQUENCE: 19

| | |
|---|---|
| gaaaaggaga agaaataaag aaagaaagaa aagagatggg tggtgacaag aaagttttca | 60 |
| ctttggctca agtgtctcag cacaacaatc ctaaagactg ttggctgatt atcggtggca | 120 |
| aggtatatga tgtgacaaag ttttggatg accatcctgg tggtgatgag gttttgttgt | 180 |
| ctgccacagg gaaggatgca actgatgatt ttgaggacgt gggtcatagc ttgagcgcta | 240 |
| gagaaatgat ggatcaatac tacgttggag agattgatcc ctcaactgtc cccaagaagg | 300 |
| ccacatataa acctccaaag cagcctcact acaatcagga taagacatct gagttcatta | 360 |
| tcaagctcct gcaattccta gttcccttttg ctatactggg tttggctttt ggtatccgcc | 420 |
| tctacacaaa atcaacttaa gatcctgatc actttcctac ggaaaacatt tcagaatcta | 480 |
| ttcctgatat aagagcctct cttagttcta gttctagttt aaatccagca attaaagctt | 540 |
| gtttctttgt tgtctcgtta tgtcattgca atccatgtct ggaatcatac tgtagacaaa | 600 |
| actgtggtgc tgatggctat cctgacttgt gtaccccagt tatgctattt acaactcttc | 660 |
| attataaaaa atgaaaaata cactaattag tcgtaaaaaa aaaaa | 705 |

<210> SEQ ID NO 20
<211> LENGTH: 678
<212> TYPE: DNA
<213> ORGANISM: Vernicia fordii

<400> SEQUENCE: 20

| | |
|---|---|
| aagatctgtt ctttctctaa ccaaaacaag aaaagaaatg ggtagttcag gaaaggtctt | 60 |
| tactttggct gaggtctctg aacacaacaa ccctaaagac tgctggcttg ttattgaggg | 120 |
| caaggtatat gatgtaacaa aattcttgga agaccatcct ggtggtgatg aggttttgct | 180 |
| ctctgccaca gggaaggatg caactgatga ttttgaggat gttggccaca gtagcagtgc | 240 |
| tagagcaatg atggatgaat tctatgttgg tgagattgat tcatcaacaa tcccttctag | 300 |
| gatggcatat actcctccta agcaacccca ctacaaccaa gacaagacaa tggagttcat | 360 |
| tatcaagttc ctccaattcg tagttcccct tctaatcttg gcttggctg ttggtatccg | 420 |
| cttctacacc aaatcagctg aagcataagt tctgaaacaa gaatcaggaa ttgaagagac | 480 |
| gaccaaaata agtttgtgtt agttatcctt ttaccttttgg ggttcttagg acatttgaat | 540 |
| tgtgcttgtt ctacctgcga ttccctttc catgtaaaat ttgatgttat catcttgttt | 600 |

```
tacttcatat gccattgaaa aacacattgc tgcttattac attacaccat tgatgatttt      660
ggaaaaaaaa aaaaaaaa                                                   678
```

<210> SEQ ID NO 21
<211> LENGTH: 25
<212> TYPE: DNA
<213> ORGANISM: Artificial Sequence
<220> FEATURE:
<223> OTHER INFORMATION: primer

<400> SEQUENCE: 21

```
aattggatcc atggcttcag atcgg                                           25
```

<210> SEQ ID NO 22
<211> LENGTH: 31
<212> TYPE: DNA
<213> ORGANISM: Artificial Sequence
<220> FEATURE:
<223> OTHER INFORMATION: primer

<400> SEQUENCE: 22

```
aattaagctt ctactctttc ttggtgtagt g                                    31
```

<210> SEQ ID NO 23
<211> LENGTH: 30
<212> TYPE: DNA
<213> ORGANISM: Artificial Sequence
<220> FEATURE:
<223> OTHER INFORMATION: primer

<400> SEQUENCE: 23

```
aattggatcc atgggttcaa aaaccaagac                                      30
```

<210> SEQ ID NO 24
<211> LENGTH: 29
<212> TYPE: DNA
<213> ORGANISM: Artificial Sequence
<220> FEATURE:
<223> OTHER INFORMATION: primer

<400> SEQUENCE: 24

```
aattaagctt tcaattttct gactcagtg                                       29
```

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25

```
aattggatcc atggcctcaa atcccaaaac                                      30
```

<210> SEQ ID NO 26
<211> LENGTH: 28
<212> TYPE: DNA
<213> ORGANISM: Artificial Sequence
<220> FEATURE:
<223> OTHER INFORMATION: primer

<400> SEQUENCE: 26

```
aattaagctt tcatgaggtg ctagcatg                                        28
```

<210> SEQ ID NO 27
<211> LENGTH: 28

```
<212> TYPE: DNA
<213> ORGANISM: Artificial Sequence
<220> FEATURE:
<223> OTHER INFORMATION: primer

<400> SEQUENCE: 27
aattgtcgac atgggtgggg agcggaac                                      28

<210> SEQ ID NO 28
<211> LENGTH: 33
<212> TYPE: DNA
<213> ORGANISM: Artificial Sequence
<220> FEATURE:
<223> OTHER INFORMATION: primer

<400> SEQUENCE: 28
aattaagctt ttatgttgat ttggtgtaga aac                                33

<210> SEQ ID NO 29
<211> LENGTH: 30
<212> TYPE: DNA
<213> ORGANISM: Artificial Sequence
<220> FEATURE:
<223> OTHER INFORMATION: primer

<400> SEQUENCE: 29
aattatcgat atgggtctag caaaggaaac                                    30

<210> SEQ ID NO 30
<211> LENGTH: 29
<212> TYPE: DNA
<213> ORGANISM: Artificial Sequence
<220> FEATURE:
<223> OTHER INFORMATION: primer

<400> SEQUENCE: 30
aattgagctc tcaatacttg ttcctgtac                                     29

<210> SEQ ID NO 31
<211> LENGTH: 29
<212> TYPE: DNA
<213> ORGANISM: Artificial Sequence
<220> FEATURE:
<223> OTHER INFORMATION: primer

<400> SEQUENCE: 31
aattatcgat atggttaaag acacaaagc                                     29

<210> SEQ ID NO 32
<211> LENGTH: 28
<212> TYPE: DNA
<213> ORGANISM: Artificial Sequence
<220> FEATURE:
<223> OTHER INFORMATION: primer

<400> SEQUENCE: 32
aattgagctc tcagtctcgg tgcgagtg                                      28

<210> SEQ ID NO 33
<211> LENGTH: 28
<212> TYPE: DNA
<213> ORGANISM: Artificial Sequence
<220> FEATURE:
<223> OTHER INFORMATION: primer

<400> SEQUENCE: 33
aattggatcc atgtcttcag atcggaag                                      28
```

```
<210> SEQ ID NO 34
<211> LENGTH: 31
<212> TYPE: DNA
<213> ORGANISM: Artificial Sequence
<220> FEATURE:
<223> OTHER INFORMATION: primer

<400> SEQUENCE: 34
aattaagctt ctagtctttc ttggtatagt g                              31

<210> SEQ ID NO 35
<211> LENGTH: 25
<212> TYPE: DNA
<213> ORGANISM: Artificial Sequence
<220> FEATURE:
<223> OTHER INFORMATION: primer

<400> SEQUENCE: 35
aattggatcc atgggcggag acgga                                     25

<210> SEQ ID NO 36
<211> LENGTH: 29
<212> TYPE: DNA
<213> ORGANISM: Artificial Sequence
<220> FEATURE:
<223> OTHER INFORMATION: primer

<400> SEQUENCE: 36
aattaagctt tcaagaagaa ggagccttg                                 29

<210> SEQ ID NO 37
<211> LENGTH: 28
<212> TYPE: DNA
<213> ORGANISM: Artificial Sequence
<220> FEATURE:
<223> OTHER INFORMATION: primer

<400> SEQUENCE: 37
aattggatcc atggcgaatc taatttcg                                  28

<210> SEQ ID NO 38
<211> LENGTH: 27
<212> TYPE: DNA
<213> ORGANISM: Artificial Sequence
<220> FEATURE:
<223> OTHER INFORMATION: primer

<400> SEQUENCE: 38
aattaagctt gttattacca acaaacg                                   27

<210> SEQ ID NO 39
<211> LENGTH: 28
<212> TYPE: DNA
<213> ORGANISM: Artificial Sequence
<220> FEATURE:
<223> OTHER INFORMATION: primer

<400> SEQUENCE: 39
aattggatcc acaagaatca aacaaaca                                  28

<210> SEQ ID NO 40
<211> LENGTH: 27
<212> TYPE: DNA
<213> ORGANISM: Artificial Sequence
<220> FEATURE:
<223> OTHER INFORMATION: primer
```

```
<400> SEQUENCE: 40
aattaagctt acttgaatct ttctctc                                    27

<210> SEQ ID NO 41
<211> LENGTH: 33
<212> TYPE: DNA
<213> ORGANISM: Artificial Sequence
<220> FEATURE:
<223> OTHER INFORMATION: primer

<400> SEQUENCE: 41
aattgcggcc gcatgggtgc aggtggaaga atg                              33

<210> SEQ ID NO 42
<211> LENGTH: 34
<212> TYPE: DNA
<213> ORGANISM: Artificial Sequence
<220> FEATURE:
<223> OTHER INFORMATION: primer

<400> SEQUENCE: 42
aaccttaatt aatcataact tattgttgta ccag                             34

<210> SEQ ID NO 43
<211> LENGTH: 34
<212> TYPE: DNA
<213> ORGANISM: Artificial Sequence
<220> FEATURE:
<223> OTHER INFORMATION: primer

<400> SEQUENCE: 43
aattgcggcc gcatggttgt tgctatggac caac                             34

<210> SEQ ID NO 44
<211> LENGTH: 33
<212> TYPE: DNA
<213> ORGANISM: Artificial Sequence
<220> FEATURE:
<223> OTHER INFORMATION: primer

<400> SEQUENCE: 44
aaccttaatt aattaattga ttttagattt gtc                              33

<210> SEQ ID NO 45
<211> LENGTH: 19
<212> TYPE: DNA
<213> ORGANISM: Artificial Sequence
<220> FEATURE:
<223> OTHER INFORMATION: primer

<400> SEQUENCE: 45
tcggaaactt cacactttt                                              19

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
tcacaaattc tggagtctta                                             20

<210> SEQ ID NO 47
<211> LENGTH: 19
```

```
<212> TYPE: DNA
<213> ORGANISM: Artificial Sequence
<220> FEATURE:
<223> OTHER INFORMATION: primer

<400> SEQUENCE: 47
tcggaaactt cacactttc                                              19

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
tcacaaattc tggagtcttg                                             20

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
atgggttcaa aaccaagac                                              20

<210> SEQ ID NO 50
<211> LENGTH: 17
<212> TYPE: DNA
<213> ORGANISM: Artificial Sequence
<220> FEATURE:
<223> OTHER INFORMATION: primer

<400> SEQUENCE: 50
tcaattttct gacttgc                                                17

<210> SEQ ID NO 51
<211> LENGTH: 19
<212> TYPE: DNA
<213> ORGANISM: Artificial Sequence
<220> FEATURE:
<223> OTHER INFORMATION: primer

<400> SEQUENCE: 51
tcaattttct gactcagtg                                              19

<210> SEQ ID NO 52
<211> LENGTH: 19
<212> TYPE: DNA
<213> ORGANISM: Artificial Sequence
<220> FEATURE:
<223> OTHER INFORMATION: primer

<400> SEQUENCE: 52
ctttgaggag gtagctaag                                              19

<210> SEQ ID NO 53
<211> LENGTH: 19
<212> TYPE: DNA
<213> ORGANISM: Artificial Sequence
<220> FEATURE:
<223> OTHER INFORMATION: primer

<400> SEQUENCE: 53
tgcgaggccc agtatcaac                                              19
```

<210> SEQ ID NO 54
<211> LENGTH: 19
<212> TYPE: DNA
<213> ORGANISM: Artificial Sequence
<220> FEATURE:
<223> OTHER INFORMATION: primer

<400> SEQUENCE: 54
ttttgaggag gtggctaat                                                  19

<210> SEQ ID NO 55
<211> LENGTH: 19
<212> TYPE: DNA
<213> ORGANISM: Artificial Sequence
<220> FEATURE:
<223> OTHER INFORMATION: primer

<400> SEQUENCE: 55
ggcaaggccc aatatcaag                                                  19

<210> SEQ ID NO 56
<211> LENGTH: 18
<212> TYPE: DNA
<213> ORGANISM: Artificial Sequence
<220> FEATURE:
<223> OTHER INFORMATION: primer

<400> SEQUENCE: 56
atgggtgggg agcggaac                                                   18

<210> SEQ ID NO 57
<211> LENGTH: 23
<212> TYPE: DNA
<213> ORGANISM: Artificial Sequence
<220> FEATURE:
<223> OTHER INFORMATION: primer

<400> SEQUENCE: 57
ttatgttgat ttggtgtaga aac                                             23

<210> SEQ ID NO 58
<211> LENGTH: 15
<212> TYPE: DNA
<213> ORGANISM: Artificial Sequence
<220> FEATURE:
<223> OTHER INFORMATION: primer

<400> SEQUENCE: 58
atgggtgggg agcgc                                                      15

<210> SEQ ID NO 59
<211> LENGTH: 28
<212> TYPE: DNA
<213> ORGANISM: Artificial Sequence
<220> FEATURE:
<223> OTHER INFORMATION: primer

<400> SEQUENCE: 59
tcatgttgat ttggtgtaga aacgaatg                                        28

<210> SEQ ID NO 60
<211> LENGTH: 22
<212> TYPE: DNA
<213> ORGANISM: Artificial Sequence
<220> FEATURE:
<223> OTHER INFORMATION: primer

```
<400> SEQUENCE: 60
cagactcgtg aacatgctct gc                                          22

<210> SEQ ID NO 61
<211> LENGTH: 22
<212> TYPE: DNA
<213> ORGANISM: Artificial Sequence
<220> FEATURE:
<223> OTHER INFORMATION: primer

<400> SEQUENCE: 61
tacctggcct tggaatactt gg                                          22
```